(12) United States Patent
Schmidtchen et al.

(10) Patent No.: US 8,227,406 B2
(45) Date of Patent: Jul. 24, 2012

(54) ANTIMICROBIAL PEPTIDES

(75) Inventors: Artur Schmidtchen, Lund (SE); Martin Malmsten, Täby (SE)

(73) Assignee: Dermagen AB, Lund (SE)

( * ) Notice: Subject to any disclaimer, the term of this patent is extended or adjusted under 35 U.S.C. 154(b) by 616 days.

(21) Appl. No.: 12/300,959

(22) PCT Filed: May 15, 2007

(86) PCT No.: PCT/SE2007/000477
§ 371 (c)(1),
(2), (4) Date: Mar. 11, 2009

(87) PCT Pub. No.: WO2007/133153
PCT Pub. Date: Nov. 22, 2007

(65) Prior Publication Data
US 2010/0159006 A1    Jun. 24, 2010

Related U.S. Application Data

(60) Provisional application No. 60/800,644, filed on May 16, 2006.

(30) Foreign Application Priority Data

May 16, 2006  (SE) ...................... 0601088

(51) Int. Cl.
*A61K 38/16* (2006.01)
(52) U.S. Cl. ......... 514/2.4; 514/3.3; 514/21.3; 514/21.4
(58) Field of Classification Search .................. None
See application file for complete search history.

(56) References Cited

U.S. PATENT DOCUMENTS

| | | | |
|---|---|---|---|
| 4,235,871 A | 11/1980 | Papahadjopoulos et al. | |
| 5,593,866 A | 1/1997 | Hancock et al. | |
| 5,646,014 A | 7/1997 | Hara | |
| 5,717,064 A | 2/1998 | Julian et al. | |
| 5,733,872 A | 3/1998 | Little | |
| 5,851,451 A | 12/1998 | Takechi et al. | |
| 5,912,230 A | 6/1999 | Oppenheim et al. | |
| 6,495,516 B1 | 12/2002 | Little, II | |
| 6,503,881 B2 | 1/2003 | Krieger et al. | |

FOREIGN PATENT DOCUMENTS

| | | |
|---|---|---|
| DE | 101 60 170 | 7/2003 |
| EP | 0 213 303 | 3/1987 |
| JP | 2004/175727 | 6/2004 |
| WO | WO 96/28468 | 9/1996 |
| WO | WO 96/38163 | 12/1996 |
| WO | WO 00/01427 | 1/2000 |
| WO | WO 01/31019 | 5/2001 |
| WO | WO 01/81578 | 11/2001 |
| WO | WO 03/018619 | 3/2003 |
| WO | WO 2004/016653 | 2/2004 |
| WO | WO 2004/058809 | 7/2004 |
| WO | WO 2004/106367 | 12/2004 |
| WO | WO 2005/001737 | 1/2005 |
| WO | WO 2005/061535 | 7/2005 |
| WO | WO 2006/035431 | 4/2006 |
| WO | WO 2006/050611 | 5/2006 |
| WO | WO 2006/054947 | 5/2006 |

OTHER PUBLICATIONS

Boman. "Innate immunity and the normal microflora." *Immunological Reviews*. vol. 173. 2000. pp. 5-16.
Lehrer et al. "Antimicrobial peptides in mammalian and insect host defense." *Immunology*. vol. II. 1999. pp. 23-27.
Tossi et al. "Amphipathic α-Helical Antimicrobial Peptides." *Biopolymers*. vol. 55. 2000. pp. 4-30.
Nordhal et al. "Domain 5 of High Molecular Weight Kininogen is Antibacterial." *Jr. of Biological Chemistry*. vol. 280. No. 41. 2005. pp. 34832-34839.
Andersson et al. "Antimicrobial activities of heparin-binding peptides." *Eur. J. Biochem*. vol. 271. 2004. pp. 1219-1226.
Boggiano et al. "Successful Identification of Novel Agents to Control Infectious Diseases from Screening Mixture-Based Peptide Combinatorial Libraries in Complex Cell-Based Bioassays." *Biopolymers*. vol. 71. No. 2. 2003. pp. 103-116.
Lehrer et al. "Ultrasensitive assays for endogenous antimicrobial polypeptides." *J. of Immun. Methods*. vol. 137. 1991. pp. 167-173.
Lequin et al. "Dermaseptin S9, an α-Helical Antimicrobial Peptide with a Hydrophobic Core and Cationic Termini." *Biochemistry*. vol. 45. 2006.. pp. 468-480.
Lohner et al. "Molecular Mechanisms of Membrane Perturbation by Antimicrobial Peptides and the Use of Biophysical Studies in the Design of Novel Peptide Antibiotics." *Comb. Chem. & High Through. Screening*. vol. 8. 2005. pp. 241-256.
Lopez-Garcia et al. "Identification of Novel Hexapeptides Bioactive against Phytopathogenic Fungi through Screening of a Synthetic Peptide Combinatorial Library." *Applied Environ. Microbiol*. vol. 68. No. 5. 2002. pp. 2453-2460.
Makovitzki et al. "Ultrashort antibacterial and antifungal lipopeptides." *PNAS*. vol. 103. No. 43. 2006. pp. 15997-16002.
Malmsten et al. "Antimicrobial peptides derived from growth factors." *Growth Factors*. vol. 25. No. I. 2007. pp. 60-70.
Ostresch et al. "Libraries from libraries: Chemical transformation of combinatorial libraries to extend the range of repertoire of chemical diversity." *Proc. Natl. Acad. Sci*. vol. 91. 1994. pp. 11138-11142.
Pasupuleti et al. "End-Tagging of Ultra-short antimicrobial peptides by W/F stretches to facilitate bacterial killing." *PLOS ONE*. vol. 4. I. 4. 2009. pp. 1-9.
Schmidtchen et al. "Boosting antimicrobial peptides by hydrophobic oligopeptide end tags." *J. Bio. Chem*. vol. 284. No. 26. 2009. pp. 17584-17594.
Sitaram. "Antimicrobial Peptides with unusual amino acid compositions and unusual structures." *Current Medicinal Chem*. vol. 13. No. 6. 2006. pp. 679-696.
Stromstedt of al. "Oligotryptophan-tagged antimicrobial peptides and the role of the cationic sequences." *Biochemica et Biophysica*. vol. 1788. No. 9. 2009. pp. 1916-1923.

*Primary Examiner* — Christina Bradley
(74) *Attorney, Agent, or Firm* — Merchant & Gould P.C.

(57) ABSTRACT

The invention relates to an antimicrobial peptide comprising a first set of amino acid residues having a length of from about 2 to about 36 amino acid residues or analogues thereof linked to the amino or carboxyterminal end a second set comprising from 3 to 8 hydrophobic amino acid residue or analogue thereof, wherein said peptide has an antimicrobial activity.

10 Claims, No Drawings

US 8,227,406 B2

ANTIMICROBIAL PEPTIDES

This application is a National Stage Application of PCT/SE2007/000477 filed 15 May 2007, which claims benefit of Serial No. 0601088-8, filed 16 May 2006 in Sweden and U.S. Ser. No. 60/800,644, filed 16 May 2006 and which applications are incorporated herein by reference. To the extent appropriate, a claim of priority is made to each of the above disclosed applications.

FIELD OF INVENTION

The invention relates to an antimicrobial peptide comprising a first set of amino acid residues having a length of from about 2 to about 36 amino acid residues or analogues thereof linked to the amino or carboxyterminal end and a second set comprising from 3 to 8 hydrophobic amino acid residues or analogues thereof, wherein said peptide has an antimicrobial activity.

BACKGROUND OF INVENTION

Several infections are successfully combated by the immune system of a mammal such as a human being. However, in some instances, bacteria, fungi, or viruses are not always cleared, which may cause localised or generalised acute infections. This is a serious concern at perinatal-, burn-, or intensive care units, and in immunocompromised individuals. Localized acute infections give rise to extensive morbidity. For example, *Pseudomonas aeruginosa* is a major cause of severe bacterial keratitis and the infection is difficult to treat successfully with the current antimicrobial agents. In other cases, a continuous bacterial persistence at epithelial surfaces may cause or aggravate chronic disease. In humans, this is exemplified by, chronic skin ulcers, atopic dermatitis and other types of eczema, acne, or genitourinary infections. For example, there is now considerable evidence that colonization or infection with the Gram-positive bacterium *Staphylococcus aureus* is a triggering or exacerbating factor in atopic dermatitis. Approximately 90% of all atopic dermatitis patients are colonized or infected by *S. aureus* whereas only 5% of healthy individuals harbour that bacterium. Chronic ulcers are colonized or infected by various bacteria, such as *P. aeruginosa*, and *S. aureus*, leading to healing delay of these ulcers.

Symptomatic infections may, be treated by various medicaments. Some diseases may also be combated by for instance vaccines. However, vaccines are not always the best treatment option and for certain microorganisms no vaccine is available. When no protection is available treatment of the disease is pursued. Often the treatment is performed by the use of an antibiotic agent, which kills the microbe. However, during the last years several microbes have become resistant against anti-biotic agents. Most likely, resistance problems will increase in the near future. Additionally, several individuals have developed allergy against the antibiotic agent, thereby reducing the possibility to effectively use certain antibiotic agents.

Epithelial surfaces of various organisms are continuously exposed to bacteria. During recent years the innate immune system, based on antibacterial peptides has been attributed important roles in the initial clearance of bacteria at biological boundaries susceptible to infection (Lehrer, R. I., and Ganz, T. (1999) *Curr Opin Immunol* 11: 23-27, Boman, H. G. (2000) *Immunol. Rev.* 173, 5-16). Antimicrobial peptides are generally thought to kill bacteria by permeating their membranes, and thus the lack of a specific molecular microbial target minimises resistance development.

Several antimicrobial peptides and proteins, unrelated to the herein, described peptides are known in the art.

U.S. Pat. No. 6,503,881 disclose cationic peptides being an indolicidin analogue to be used as an antimicrobial peptide. The cationic peptides being derived from different species, including animals and plants.

U.S. Pat. No. 5,912,230 disclose anti-fungal and anti-bacterial histatin-based peptides. The peptides being based on defined portions of the amino acid sequences of naturally occurring human histatins and methods for treatment of fungal and bacterial infections.

U.S. Pat. No. 5,717,064 disclose methylated lysine-rich lytic peptides. The lytic peptides being tryptic digestion resistant and non-natural. The lytic peptides are suitable for in vivo administration.

U.S. Pat. No. 5,646,014 disclose an antimicrobial peptide. The peptide was isolated from an antimicrobial fraction from silkworm hemolymph. The peptide exhibits excellent antimicrobial activity against several bacterial strains, such as *Escherichia coli, Staphylococcus aureus* and *Bacillus cereus*.

WO2004016653 discloses a peptide based on the 20-44 sequence of azurocidin. This peptide contains a loop structure linked by disulfide bridges.

U.S. Pat. No. 6,495,516 and related patents, disclose peptides based on the bactericidal 55 kDa protein bactericidal/permeability increasing protein (BPI). The peptides exerted antimicrobial effects as well as had LPS-neutralising capacity.

WO 01/81578 discloses numerous sequences encoding G-coupled protein-receptor related polypeptides, which may be used for numerous diseases.

At present, over 700 different antimicrobial peptide sequences are known (www.bbcm.univ.trieste.it/~tossi/search.htm), including cecropins, defensins magainins and cathelicidins.

Even though there are a relatively large number of antimicrobial peptides available today there is still an increased need of new improved antimicrobial peptides, which can be used to combat microbes, microbes which are resistant or tolerant against antibiotic agents and/or other antimicrobial agents. More importantly, there is a need for new antimicrobial peptides, which are non-allergenic when introduced into mammals such as human beings.

Due to potential lytic as well as other properties of AMPs against bacterial as well as mammalian membranes, one of the challenges in designing new peptides relies on developing AMPs with high specificity against microorganisms such as bacterial or fungal cells, i.e., a high therapeutic index (minimal hemolytic concentration/minimal antimicrobial activity; MHC/MEC).

Various bacteria, such as *P. aeruginosa, E. faecalis, Proteus mirabilis, Streptococcus pyogenes* and *S. aureus* all secrete proteases that degrade several antimicrobial peptides, such as the cathelicidin LL-37. Thus, protease resistant antimicrobial peptides are advantageous from a theraputical standpoint. Additionally, many of the antimicrobial peptides are not very efficient in challenging microorganisms such as bacteria, e.g., *S. aureus* and *P. aeruginosa*, frequently playing key roles in problematic patogeneses, and needs to be optimised to show an increased effect.

SUMMARY OF THE INVENTION

The invention relates to new improved antimicrobial peptides having an increased antimicrobial activity compared to the corresponding peptide. It has surprisingly been found that there is a specific numbers of amino acids required to increase the antimicrobial activity, i.e., if there is less than 3 or more than 8 amino acid residues the antimicrobial activity is decreased. The approach is particularly suitable for hydrophilic, highly positively charged, peptides, since these are highly membrane-disruptive. It might be that by modifying the peptide with one or several hydrophobic amino acids, their binding capacity to the lipid membrane(s) of bacteria is enhanced, and the resulting higher peptide binding results in enhanced defect formation of the membrane of the microorganism, and in higher mortality of the microorganism. However, this is only a theory and the mode of action may be different or being a combination of different mode of actions.

In a first aspect, the invention relates to an antimicrobial peptide comprising a first set of amino acid residues having a length of from about 2 to about 36 amino acid residues or analogues thereof linked to the amino or carboxyterminal end a second set comprising from 3 to 8 hydrophobic amino acid residue or analogue thereof, wherein said peptide obtains an antimicrobial activity or an improved antimicrobial activity.

In another aspect, the invention relates to an antimicrobial/pharmaceutical composition comprising the antimicrobial peptide and an acceptable buffer, diluent, carrier, adjuvant or excipient.

In a further aspect the invention also relates to a product comprising said antimicrobial peptide, said being selected from the group consisting of bandages, plasters, sutures, soap, tampons, diapers, shampoos, tooth paste, anti-acne compounds, suncreams, textiles, coating of catheters and needles, contact lenses, adhesives, incorporated in wound dressings, cleaning solutions or implants.

In another aspect the invention relates to the use of the antimicrobial peptide or the antimicrobial/pharmaceutical composition or the product in therapy or diagnosis.

In a final aspect, the invention relates to the use of the antimicrobial peptide, antimicrobial/pharmaceutical composition or a product comprising said antimicrobial peptide for the manufacture of a medicament for the treatment of an antimicrobial disease or infection, caused by a microorganism selected from the group consisting of bacteria, virus, parasites, fungus and yeast.

By providing such antimicrobial peptides, the risks for allergic reactions to antimicrobial peptides may be reduced due to the fact that the peptides may be derived from the polypeptide sequence of endogenous proteins and/or peptides or having a similar amino acid residue composition. By using short peptides the stability of the peptide is increased and the production costs reduced, as compared to longer peptides and proteins, whereby the invention may be economically advantageous.

The peptides of the invention provide compositions, which facilitate efficient prevention, reduction or elimination of microorganisms. Thereby the possibility to combat microorganisms, which are resistant or tolerant against the antibiotic agents, may be increased. Moreover, mammals, which are allergic against commercially available antimicrobial agents, may be treated. By providing antimicrobial/pharmaceutical compositions, which are derived from endogenous improved proteins, the probability may be reduced or even eliminated that a mammal will develop allergy against these particular peptides. This makes the antimicrobial/pharmaceutical compositions useful for several applications in which the antimicrobial/pharmaceutical compositions contact a mammal either as a medicament or as an additive to prevent infections.

Additionally, the use of short peptides may improve bioavailability. Furthermore, the use of structurally distinct peptides with specific or preferable actions on Gram-negative and Gram-positive bacteria, or fungi, enables specific targeting of various microorganisms, thus minimising development of resistance and ecological problems. By using supplementing peptides, which are comparable to peptides already existing in the mammal, the risk of additional ecological pressure by novel antibiotics is further diminished. Finally, these formulations may also enhance the effect of endogenous antimicrobial peptides or analogous thereof.

The inventive antimicrobial peptides increase the list of antimicrobial agents, which aid in the choice to prevent, reduce or eliminate microorganisms in all kind of applications including but not limited to those that invade or infect mammals, such as the human being.

DETAILED DESCRIPTION OF THE INVENTION

Definitions

In the context of the present application and invention the following definitions apply:

The term "nucleotide sequence" is intended to mean a sequence of two or more nucleotides. The nucleotides may be of genomic DNA, cDNA, RNA, semisynthetic or synthetic origin or a mixture thereof. The term includes single and double stranded forms of DNA or RNA.

The term "antimicrobial composition" is intended to mean any composition containing the invented peptides according to the invention, such as antimicrobial or pharmaceutical compositions useful to combat microorganisms, which attack mammals as well as compositions comprising one or more additional antimicrobial agents such as antibiotics as well as other agents.

The term "substituted" is intended to mean that an amino acid residue is replaced by another amino acid residue.

The term "analogues thereof" is intended to mean that part of or the entire peptide is based on non protein amino acid residues (synthetic or semisynthetic), such as aminoisobutyric acid (Aib), norvaline gamma-aminobutyric acid (Abu) or ornithine. Examples of other non protein amino acid residues can be found at http://www.hort.purdue.edu/rhodcv/hort640c/polyam/po00008.htm.

The term "removed" is intended to mean that at least one amino acid residue has been removed, i.e., released from the polypeptide without being replaced by another amino acid residue.

The term "homology" is intended to mean the overall homology of the polypeptide, not to be mixed up with the word "similarities" meaning that specific amino acid residues belong to the same group (i.e hydrophobic, hydrophilic), or "identity", meaning that amino acid residues are identical.

The term "linked" is intended to mean "linked" with covalent or chemical bonds.

The term "antimicrobial peptide" is intended to mean a peptide, which prevents, inhibits, reduces or destroys a microorganism. The antimicrobial activity can be determined by any method, such as the method in EXAMPLE 1.

The term "amphipathic" is intended to mean the distribution of hydrophilic and hydrophobic amino acid residues along opposing faces of an α-helix structure, β-strand, linear, circular, or other secondary conformation, as well as along the peptide primary structure, which result in one or several domains of the molecule being predominantly charged and hydrophilic and the other being predominantly hydrophobic.

The term "cationic" is intended to mean a molecule, which has a net positive charge within the pH range of from about 2 to about 12, such as within the range from about 4 to about 10.

The term "microorganism" is intended to mean any living microorganism. Examples of microorganisms are bacteria, fungi, virus, parasites and yeasts.

The term "antimicrobial agent" is intended to mean any agent, which prevent, inhibit or destroy life of microbes. Examples of antimicrobial agents can be found in The Sanford Guide to Antimicrobial Therapy (32nd edition, Antimicrobial Therapy, Inc, US).

In the present context, amino acid names and atom names are used as defined by the Protein DataBank (PNB) (www.p-db.org), which is based on the IUPAC nomenclature (IUPAC Nomenclature and Symbolism for Amino Acids and Peptides (residue names, atom names etc.), Eur J Biochem., 138, 9-37 (1984) together with their corrections in Eur J Biochem., 152, 1 (1985). The term "amino acid" is intended to indicate an amino acid from the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W) and tyrosine (Tyr or Y), or derivatives thereof.

Description

Antimicrobial Peptide

In a first embodiment the invention relates to an antimicrobial peptide comprising a first set of amino acid residues having a length of from about 2 to about 36 amino acid residues or analogues thereof linked to a second set comprising at least one hydrophobic amino acid residue or analogue thereof, wherein said peptide obtains an antimicrobial activity or an increased antimicrobial activity. By linking a second set of amino acid residues, wherein the amino acid residues are hydrophobic the antimicrobial activity of the peptide is improved/increased or obtained. By the use of a combination of a first and a second set of amino acid residues, in which the second set comprises hydrophobic amino acid residues it is even possible to make an inactive first set of amino acid residues active against microorganisms. The first set of amino acid residues has affinity to microorganism only or may possess antimicrobial activity.

The second set of hydrophobic amino acid residues may be 3, 4, 5, 6, 7 or 8 amino acid residues or analogues thereof and the hydrophobic amino acid residues may be selected from the group consisting of V, L, I, F, Y and W. The second set of hydrophobic amino acid residues may comprise one and the same hydrophobic amino acid residues, such as a set of W or F or be a mixture of different hydrophobic amino acid residues as well as D amino acid residues or synthetic amino acid residues as long as they are hydrophobic. The second set of amino acid residues may be linked to the first set of amino acid residues at the C- or N-terminal or at both ends of said first set of amino acid residues. Examples of the second sets of three to eight amino acid residues are $F_{(3-8)}$ (SEQ ID NO:155), $W_{(3-8)}$ (SEQ ID NO:156), $I_{(3-8)}$ (SEQ ID NO:157), $Y_{(3-8)}$ SEQ ID NO:158), $V_{(3-8)}$ (SEQ ID NO:159), and mixtures of said amino acid residues or analogues thereof. $F_{(3-8)}$ (SEQ ID NO:155) is intending to mean that there is from 3 to 8 F present in the second set of hydrophobic amino acid residues, i.e., 3, 4, 5, 6, 7 or 8 amino acid residues being one and the same or a mixture thereof as well as analogues thereof. Examples of mixtures of amino acid residues are FWY, WWYYII (SEQ ID NO:160), WYIV (SEQ ID NO:161), YYVVFF (SEQ ID NO:162) etc, i.e., the most important aspect being that the end is a hydrophobic end being linked to the other part and thereby enabling an increased antimicrobial activity. It has also surprisingly been found that there is a specific numbers of amino acids required to increase the antimicrobial activity, i.e., if there is less than 3 or more than 8 amino acid residues the antimicrobial activity is decreased. The first set may be a linear structure with amino acid residues, such as cationic amino acids or other amino acid residues which give rise to a linear structure. The first set of amino acid residues may in total have a positive net charge.

The first set of amino acid residues may be obtained from any source as long as the first set of amino acid residues show binding to microorganism or antimicrobial activity or may be antimicrobial when combined with the second set of amino acid residues. The first set of amino acid residues may be synthetic as well as semisynthetic as well as native. Examples of proteins from which the first set of amino acid residues are derived are kininogen proteins, growth factor proteins, histidine rich glycoprotein, coagulation factor proteins such as thrombin, factor IX and X, complement factor C3a, von Willebrand factor, vitronectin, protein C inhibitor, fibronectin, chemokines, laminin, superoxide dismutase, prion proteins, or PRELP (proline arginine-rich end leucine-rich repeat protein). Another example is the first set of amino acid residues derived from SEQ ID NO 1 or the sequences found in the table as well as SEQ ID NO 2-12. The size of the first set of amino acid residues may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acid residues or analogous thereof.

Additionally the peptide may be substituted in one or more amino acid residues, such as from 2-21 amino acid residues. For example 3, 4, 5, 6, 7, 8, 9, 10, 11, 12, 13, 14, 15, 16, 17, 18, 19 or 20 amino acid residues may be removed and/or substituted.

The antimicrobial peptides may be extended by one or more amino acid residues, such as 1-100 amino acid residues, 5-50 amino acid residues or 6, 7, 8, 9, 10, 11, 12, 13, 14, 15, 16, 17, 18, 19, 20, 21, 22, 23, 24, 25, 26, 27, 28, 29 or 30 amino acid residues. Such additional amino acids may duplicate a sequence contiguous to the sequence of the antimicrobial peptide derived from a non-antimicrobial protein. The number to be added depends on which microorganism to be combated in including, stability of the peptide, toxicity, the mammal to be treated or in which product the peptide should be in and which peptide structure the antimicrobial peptide is based upon. The number of amino acid residues to be added to the peptides depends also on the choice of production, e.g., expression vector and expression hosts and the choice of manufacturing the antimicrobial/pharmaceutical composition. The extension may be at the N- or C-terminal part or at both parts of the antimicrobial peptides as long as it does not disrupt the antimicrobial effect of the peptide. The antimicrobial peptides may also be a fusion protein, wherein the antimicrobial peptide is fused to another peptide.

Additionally the antimicrobial peptides may be operably linked to other known antimicrobial peptides or other substances, such other peptides, lipids, proteins, oligosaccharides, polysaccharides, other organic compounds, or inorganic substances. For example the antimicrobial peptides may be coupled to a substance which protect the antimicrobial peptides from being degraded within a mammal prior to the antimicrobial peptides has inhibited, prevented or destroyed the life of the microorganism.

Accordingly the antimicrobial peptides may be modified at the C-terminal part by amidation or esterification and at the N-terminal part by acylation, acetylation, PEGylation, alkylation and the like.

Examples of microorganisms that are inhibited, prevented or destroyed by the antimicrobial peptide are bacteria, both Gram positive and Gram-negative bacteria such as *Enterococcus faecalis, Eschericia coli, Pseudomonas aeruginosa, Proteus mirabilis, Streptococcus pneumoniae, Streptococcus pyogenes, Staphylococcus aureus, Finegoldia magna, Helicobacter pylorii*, viruses, parasites, fungus and yeast, such as *Candida albicans* and *Candida parapsilosi* as well as *Malassezia* species. Other microorganisms of interest include, but are not limited to *Citrobacter* sp., *Klebsiella* sp., *Enterobacter* sp., *Morganella, Providencia, Listeria* sp., *Salmonella* sp., *Serratia* sp., *Shigella* sp., *Yersinia* sp., *Pasteurella* sp., *Vibrio* sp., *Campylobacter* sp., *Haemophilus* sp., *Bordetella* sp., *Brucella* sp., *Neiserria* sp., *Legionella* sp., *Mycoplasma* sp., and *Chalmydia* sp. Other examples are virus, such as Herpes Simplex, Varizella Zooster, Influenza viruses. Examples of parasites are endo- and ectoparasites, including *plasmodium* forms.

The antimicrobial peptides may be obtained from a naturally occurring source, such as from a human cell, a c-DNA, genomic clone, chemically synthesised or obtained by recombinant DNA techniques as expression products from cellular sources.

The antimicrobial peptides may be synthesised by standard chemical methods, including synthesis by automated procedure. In general, peptide analogues are synthesised based on the standard solid-phase Fmoc protection strategy with HATU (N-[DIMETHYLAMINO-1H-1,2,3,-TRIAZOLO[4,5-B]PYRIDIN-1-YLMETHYLELE]-N-METHYL-METHANAMINIUM HEXAFLUOROPHOSPHATE N-OXIDE) as the coupling agent or other coupling agents such as HOAt-1-HYDROXY-7-AZABENZOTRIAZOLE. The peptide is cleaved from the solid-phase resin with trifluoroacetic acid containing appropriate scavengers, which also deprotects side chain functional groups. Crude peptide is further purified using preparative reversed-phase chromatography. Other purification methods, such as partition chromatography, gel filtration, gel electrophoresis, or ion-exchange chromatography may be used. Other synthesis techniques, known in the art, such as the tBoc protection strategy, or use of different coupling reagents or the like can be employed to produce equivalent peptides.

Peptides may alternatively be synthesised by recombinant production (see e.g., U.S. Pat. No. 5,593,866). A variety of host systems are suitable for production of the peptide analogues, including bacteria, such as *E. coli*, yeast, such as *Saccharomyces cerevisiae* or *pichia*, insects, such as Sf9, and mammalian cells, such as CHO or COS-7. There are many expression vectors available to be used for each of the hosts and the invention is not limited to any of them as long as the vector and host is able to produce the antimicrobial peptide. Vectors and procedures for cloning and expression in *E. coli* can be found in for example Sambrook et al. (Molecular Cloning.: A Laboratory Manual, Cold Spring Harbor Laboratory Press, Cold Spring Harbor, N.Y., 1987) and Ausubel et al. (Current Protocols in Molecular Biology, Greene Publishing Co., 1995).

Finally, the peptides may be purified from plasma, blood, various tissues or the like. The peptides may be endogenous, or generated after enzymatic or chemical digestion of the purified protein. For example, a protein may be digested by trypsin and the resulting antibacterial peptides further isolated in larger scale.

A DNA sequence encoding the antimicrobial peptide is introduced into a suitable expression vector appropriate for the host. In preferred embodiments, the gene is cloned into a vector to create a fusion protein. To facilitate isolation of the peptide sequence, amino acids susceptible to chemical cleavage (e.g., CNBr) or enzymatic cleavage (e.g., V8 protease, trypsin) are used to bridge the peptide and fusion partner. For expression in *E. coli*, the fusion partner is preferably a normal intracellular protein that directs expression toward inclusion body formation. In such a case, following cleavage to release the final product, there is no requirement for renaturation of the peptide. In the present invention, the DNA cassette, comprising fusion partner and peptide gene, may be inserted into an expression vector. Preferably, the expression vector is a plasmid that contains an inducible or constitutive promoter to facilitate the efficient transcription of the inserted DNA sequence in the host.

The expression vector can be introduced into the host by conventional trans-formation techniques such as by calcium-mediated techniques, electroporation, or other methods well known to those skilled in the art.

The sequence encoding the antimicrobial peptide may be derived from a natural source such as a mammalian cell, an existing cDNA or genomic clone or synthesised. One method, which may be used, is amplification of the antimicrobial peptide by the aid of PCR using amplification primers which are derived from the 5' and 3' ends of the antimicrobial DNA template and typically incorporate restriction sites chosen with regard to the cloning site of the vector. If necessary, translational initiation and termination codons can be engineered into the primer sequences. The sequence encoding the antimicrobial peptide may be codon-optimised to facilitate expression in the particular host as long as the choice of the codons are made considering the final mammal to be treated. Thus, for example, if the antimicrobial peptide is expressed in bacteria, the codons are optimised for bacteria.

The expression vector may contain a promoter sequence, to facilitate expression of the introduced antimicrobial peptide. If necessary, regulatory sequences may also be included, such as one or more enhancers, ribosome binding site, transcription termination signal sequence, secretion signal sequence, origin of replication, selectable marker, and the like. The regulatory sequences are operably linked to each other to allow transcription and subsequent translation. If the antimicrobial peptide is o be expressed in bacteria, the regulatory sequences are those which are designed to be used within bacteria and such are well-known for a person skilled in the art. Suitable promoters, such as constitutive and inducible promoters, are widely available and include promoters from T5, T7, T3, SP6 phages, and the trp, 1 pp, and lac operons.

If the vector containing the antimicrobial peptide is to be expressed within bacteria examples of origin are either those, which give rise to a high copy number or those which give rise to a low copy, for example f1-ori and col E1 ori.

Preferably, the plasmids include at least one selectable marker that is functional in the host, which allows transformed cells to be identified and/or selectively grown. Suitable selectable marker genes for bacterial hosts include the ampicillin resistance gene, chloramphenicol resistance gene, tetracycline resistance gene, kanamycin resistance gene and others known in the art.

Examples of plasmids for expression in bacteria include the pET expression vectors pET3a, pET 11a, pET 12a-c, and pET 15b (available from Novagen, Madison, Wis.). Low copy number vectors (e.g., pPD 100) can be used for efficient overproduction of peptides deleterious to the *E. coli* host (Dersch et al., FEMS Microbiol. Lett. 123:19, 1994).

Examples of suitable hosts are bacteria, yeast, insects and mammal cells. However, often either bacteria such as *E. coli* is used.

The expressed antimicrobial peptide is isolated by conventional isolation techniques such as affinity, size exclusion, or ionic exchange chromatography, HPLC and the like. Different purification techniques can be found in A Biologist's Guide to Principles and Techniques of Practical Biochemistry (eds. Wilson and Golding, Edward Arnold, London, or in Current Protocols in Molecular Biology (John Wiley & Sons, Inc).

Accordingly, the peptides may bind and inactivate lipopolysaccharides from various Gram-negative bacteria, thus acting as inhibitors of lipopolysaccharide-induced inflammation. The peptides may also modulate growth of eukaryotic cells. The invented antimicrobial peptide may be placed/integrated in a product such as bandages, plasters, sutures, soap, tampons, diapers, shampoos, tooth paste, anti-acne compounds, suncreams, textiles, adhesives, incorporated in wound dressings, cleaning solutions, contact lenses or implants.

Additionally, the invention relates to pharmaceutical compositions comprising an antimicrobial peptide as described above and a pharmaceutical acceptable buffer, diluent, carrier, adjuvant or excipient. Additional compounds may be included in the compositions, such as other antimicrobial peptides, immunomodulating agents, antipruritus agents. Examples of other antimicrobial peptides are disclosed in WO 2005/061535 and WO 2005/001737. Other examples include, chelating agents such as EDTA, citrate, EGTA or glutathione. The antimicrobial/pharmaceutical compositions may be prepared in a manner known in the art that is sufficiently storage stable and suitable for administration to humans and animals. The pharmaceutical compositions may be lyophilised, e.g., through freeze drying, spray drying or spray cooling.

"Pharmaceutically acceptable" means a non-toxic material that does not decrease the effectiveness of the biological activity of the active ingredients, i.e., the antimicrobial peptide(s). Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition.

The excipient may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The invented formulation may also contain one or more mono- or disaccharides such as xylitol, sorbitol, mannitol, lactitiol, isomalt, maltitol or xylosides, and/or monoacylglycerols, such as monolaurin. The characteristics of the carrier are dependent on the route of administration. One route of administration is topical administration. For example, for topical administrations, a preferred carrier is an emulsified cream comprising the active peptide, but other common carriers such as certain petrolatum/mineral-based and vegetable-based ointments can be used, as well as polymer gels, liquid crystalline phases and microemulsions.

The compositions may comprise one or more peptides, such as 1, 2, 3 or 4 different peptides. By using a combination of different peptides the antimicrobial effect may be increased and/or the possibility that the microorganism might be resistant and/or tolerant against the antimicrobial agent.

The peptide as a salt may be an acid adduct with inorganic acids, such as hydrochloric acid, sulfuric acid, nitric acid, hydrobromic acid, phosphoric acid, perchloric acid, thiocyanic acid, boric acid etc. or with organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid etc. Inorganic salts such as monovalent sodium, potassium or divalent zinc, magnesium, copper calcium, all with a corresponding anion, may be added to improve the biological activity of the antimicrobial composition.

The antimicrobial/pharmaceutical compositions of the invention may also be in the form of a liposome, in which the peptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Preparation of such liposomal formulations is can be found in for example U.S. Pat. No. 4,235,871.

The antimicrobial/pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(carprolactone) (PCL), and polyanhydrides have been widely used as biodegradable polymers in the production of microshperes. Preparations of such microspheres can be found in U.S. Pat. No. 5,851,451 and in EP0213303.

The antimicrobial/pharmaceutical compositions of the invention may also be in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the peptide. The polymers may also comprise gelatin or collagen.

Alternatively, the antimicrobial peptides may be dissolved in saline, water, polyethylene glycol, propylene glycol, ethanol or oils (such as safflower oil, corn oil, peanut oil, cottonseed oil or sesame oil), tragacanth gum, and/or various buffers. The pharmaceutical composition may also include ions and a defined pH for potentiation of action of antimicrobial peptides.

The antimicrobial/pharmaceutical compositions may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

The pharmaceutical compositions according to the invention may be administered locally or systemically. Routes of administration include topical, ocular, nasal, pulmonar, buccal, parenteral (intravenous, subcutaneous, and intramuscular), oral, parenteral, vaginal and rectal. Also administration from implants is possible. Suitable preparation forms are, for example granules, powders, tablets, coated tablets, (micro) capsules, suppositories, syrups, emulsions, microemulsions, defined as optically isotropic thermodynamically stable systems consisting of water, oil and surfactant, liquid crystalline phases, defined as systems caracterised by long-range order but short-range disorder (examples include lamellar, hexagonal and cubic phases, either water- or oil continuous), or their dispersed counterparts, gels, ointments, dispersions, suspensions, creams, aerosols, droples or injectable solution in ampule form and also preparations with protracted release of active compounds, in whose preparation excipients, diluents, adjuvants or carriers are customarily used as described above. The pharmaceutical composition may also be provided in bandages, plasters or in sutures or the like.

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the, activity of the compound, manner of administration, nature and severity of the disorder, age and body weight of the patient different doses may be needed. The administration of the dose can be carried out both by single administration in the form of an individual dose unit or else several smaller dose units and also by multiple administration of subdivided doses at specific intervals The pharmaceutical compositions of the invention may be administered alone or in combination with other therapeutic agents, such as antibiotic, antiinflammatory or antiseptic agents such as anti-bacterial agents, anti-fungicides, anti-viral agents, and anti-parasitic agents. Alternatively, the pharmaceutical composition comprises one or more antibiotic or antiseptic agent(s). Examples are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide. These agents may be incorporated as part of the same pharmaceutical composition or may be administered separately. The pharmaceutical compositions may also contain anti-inflammatory drugs such as steroids and macrolactam derivatives.

The present invention concerns both humans and other mammal such as horses, dogs, cats, cows, pigs, camels, among others. Thus the methods are applicable to both human therapy and veterinary applications. The objects, suitable for such a treatment may be identified by well-established hallmarks of an infection, such as fever, puls, culture of organisms, and the like. Infections that may be treated with the antimicrobial peptides include those caused by or due to microorganisms. Examples of microorganisms include bacteria (e.g., Gram-positive, Gram-negative), fungi, (e.g., yeast and molds), parasites (e.g., protozoans, nematodes, cestodes and trematodes), viruses, and prions. Specific organisms in these classes are well known (see for example, Davis et al., Microbiology, 3.sup.rd edition, Harper & Row, 1980). Infections include, but are not limited to, chronic skin ulcers, infected acute acute and chronic wounds and burn wounds, infected skin eczema, impetigo, atopic dermatitis, acne, external otitis, vaginal infections, seborrhoic dermatitis, oral infections and parodontitis, candidal intertrigo, conjunctivitis and other eye infections such as *P. aeruginosa* keratitis, and pneumonia.

Accordingly, the pharmaceutical compositions may be used for prophylactic treatment of burn wounds, after surgery and after skin trauma. The pharmaceutical composition may also be included in solutions intended for storage and treatment of external materials in contact with the human body, such as contact lenses, orthopedic implants, and catheters.

Additionally, the pharmaceutical compositions may be used for treatment of atopic dermatitis, impetigo, chronic skin ulcers, infected acute wound and burn wounds, acne, external otitis, fungal infections, pneumonia, seborrhoic dermatitis, candidal intertrigo, candidal vaginitis, oropharyngeal candidiasis, eye infections (bacterial conjunctivitis), and nasal infections (including MRSA carriage).

The pharmaceutical compositions may also be used to in cleansing solutions, such as lens disinfectants and storage solutions or used to prevent bacterial infection in association with urinary catheter use or use of central venous catheters.

Additionally, the compositions may be used for prevention of infection postsurgery in plasters, adhesives, sutures, or be incorporated in wound dressings.

The antimicrobial peptides may also be used in polymers, textiles or the like to create antibacterial surfaces or cosmetics, and personal care products (soap, shampoos, tooth paste, anti-acne, suncreams, tampons, diapers, etc) may be supplemented with the pharmaceutical compositions.

Finally, the invention relates to a method of treating a mammal having a microbial infection or suffering from allergy comprising administering to a patient a therapeutically effective amount of the pharmaceutical composition defined above.

Following examples are intended to illustrate, but not to limit, the invention in any manner, shape, or form, either explicitly or implicitly.

EXAMPLES

Antimicrobial Peptides

Peptides. Peptides were from Sigma-Genosys, generated by a peptide synthesis platform (PEPscreen®, Custom Peptide Libraries, SigmaGenosys). Yield was ~1-6 mg, and peptide length 20 amino acids. MALDI-ToF Mass Spectrometry was perfomed on these peptides. Average Crude Purity of 20mers was ~60%. Peptides were supplied lyophilized and in a 96-well tube rack. Prior to biological testing the PEPscreen peptides were diluted in dH$_2$O (5 mM stock), and stored at −20 C. This stock solution was used for the subsequent experiments.

Microorganisms

Eschericia coli ATCC25922, *Staphylococcus aureus* ATCC29213, and the fungal isolate *Candida albicans* ATCC90028 were obtained from the Department of Bacteriology, Lund University Hospital.

Example 1

Radial Diffusion Assay

Radial diffusion assays (RDA) were performed essentially as described earlier (Lehrer, R. I., Rosenman, M., Harwig, S. S., Jackson, R. & Eisenhauer, P. (1991) Ultrasensitive assays for endogenous antimicrobial polypeptides, *J Immunol Methods*. 137, 167-73). Results are shown in Table 1 a-e. Briefly, bacteria (*E. coli, S. aureus*) or fungi (*C. albicans*) were grown to midlogarithmic phase in 10 ml of full-strength (3% w/v) trypticase soy broth (TSB) (Becton-Dickinson, Cockeysville, Md.). The microorganisms were washed once with 10 mM Tris, pH 7.4. 4×10$^6$ bacterial cfu or 1×10$^5$ fungal cfu was added to 5 ml of the underlay agarose gel, consisting of 0.03% (w/v) TSB, 1% (w/v) low-electroendoosmosistype (Low-EEO) agarose (Sigma, St Louise Mo.) and a final concentration of 0.02% (v/v) Tween 20 (Sigma). The underlay was poured into a Ø 85 mm petri dish. After agarose solidified, 4 mm-diameter wells were punched and 6 µl of test sample was added to each well. Plates were incubated at 37° C. for 3 hours to allow diffusion of the peptides. The underlay gel was then covered with 5 ml of molten overlay (6% TSB and 1% Low-EEO agarose in dH$_2$O). Antimicrobial activity of a peptide is visualized as a clear zone around each well after 18-24 hours of incubation at 37° C. for bacteria and 28° C. for *Candida albicans*. Other examples of peptides that were screened and found to show an increased effect against the above mentioned microorgansism are listed below. Some of the results are found in table 1c showing the effects against *C. albicans*, table 1d *E. coli* and table 1e *S. aureus*.

```
Complement
CNY1                                                (SEQ ID
                                                    NO. 137)
CNY1WWW      CNYITELRRQHARASHLGLAWWW                (SEQ ID
                                                    NO. 138)
CNY187       (SEQ ID
             NO. 139)
CNY187WWW    CKYILLLRRQHARAWRRGLRWWW                (SEQ ID
                                                    NO. 140)

Growth fac-
tors
GKR22                                               (SEQ ID
                                                    NO. 141)
GKR22WWW     GKRKKKGKGLGKKRDPCLRKYKWWW              (SEQ ID
                                                    NO. 142)

PKR21        (SEQ ID
             NO. 143)
PKR21WWW     PKRKKKGGKNGKNRRNRKKKNWWW               (SEQ ID
                                                    NO. 144)

Coagulation-
factor II
VFR17                                               (SEQ ID
                                                    NO. 145)
VER17WWW     VFRLKKWIQKVIDQFGEWWW                   (SEQ ID
                                                    NO. 146)

Protein C in-
hibitor
SEK20                                               (SEQ ID
                                                    NO. 147)
SEK20WWW     SEKTLRKWLKMFKKRQLELYWWW                (SEQ ID
                                                    NO. 148)

PRELP
QPT22                                               (SEQ ID
                                                    NO. 149)
QPT22WWW     QPTRRPRPGTGPGRRPRPRPRPWWW              (SEQ ID
                                                    NO. 150)

LL-37
LL-37                                               (SEQ ID
                                                    NO. 151)
LL-37WWW     LLGDFFRKSKEKI                          (SEQ ID
             KEFKRIVQRIKDFLRNLVPRTESWWW             NO. 152)

Omiganan     (SEQ ID
             NO. 153)
OmigananWWW  ILRWPWWPWRRKWWW                        (SEQ ID
                                                    NO. 154)
```

Example 2

Hemolysis Assay

EDTA-blood was centrifuged at 800 g for 10 min, whereafter plasma and buffy coat were removed. The erythrocytes were washed three times and resuspended in 5% PBS, pH 7.4. The cells were then incubated with end-over-end rotation for 1 h at 37° C. in the presence of peptides (3-60 µM). 2% Triton X-100 (Sigma-Aldrich) served as positive control. The samples were then centrifuged at 800 g for 10 min. The absorbance of hemoglobin release was measured at λ 540 nm and is in the plot expressed as % of TritonX-100 induced hemolysis (Table 1a).

TABLE 1a

| SEQ ID No | Peptide Nr Sequence | E.coli ATCC 25922 24/04/2066 Mean Ingrowth* | SD | E.coli ATCC 25922 24/04/2066 Mean Ingrowth | SD | S. aureus ATCC 29213 21/04/2006 Mean | SD | Candida albicans ATCC 90028 22/04/2006 Mean | SD | Hemolysis (%) 20/04/2006 Mean | SD |
|---|---|---|---|---|---|---|---|---|---|---|---|
| 13 | 1. HKHGHGHGKHKNKGKKN | 0.947 | 0.526 | 0.947 | 0.526 | 0.747 | 0.382 | 1.493 | 0.516 | 2.321 | 0.057 |
| 14 | 2. LHKHGHGHGKHKNKGKKN | 7.277 | 0.200 | 2.320 | 0.299 | 1.963 | 0.547 | 0.920 | 0.185 | 2.382 | 0.022 |
| 15 | 3. LLHKHGHGHGKHKNKGKKN | 5.977 | 0.474 | 2.820 | 0.095 | 2.900 | 0.332 | 1.927 | 0.555 | 2.394 | 0.059 |
| 16 | 4. LLLHKHGHGHGKHKNKGKKN | 7.450 | 0.385 | 5.933 | 0.352 | 3.607 | 0.179 | 4.483 | 0.382 | 2.425 | 0.059 |
| 17 | 5. HKHGHGHGKHKNKGKKNL | 5.613 | 0.939 | 2.650 | 0.275 | 2.903 | 0.451 | 3.167 | 0.817 | 2.255 | 0.051 |
| 18 | 6. HKHGHGHGKHKNKGKKNLL | 6.060 | 0.686 | 3.753 | 0.341 | 3.763 | 0.309 | 3.313 | 0.291 | 2.431 | 0.063 |
| 19 | 7. HKHGHGHGKHKNKGKKNLLL | 6.893 | 0.535 | 4.940 | 1.161 | 5.710 | 0.665 | 4.723 | 0.731 | 2.418 | 0.058 |
| 20 | 8. HKHGHGHGLKHKNKGKKN | 6.597 | 1.067 | 2.833 | 0.459 | 2.803 | 0.399 | 2.713 | 0.388 | 2.509 | 0.060 |
| 21 | 9. HKHGHGHGLLKHKNKGKKN | 5.727 | 0.726 | 3.637 | 0.253 | 2.907 | 0.320 | 3.053 | 0.427 | 2.546 | 0.064 |
| 22 | 10. HKHGHGHGLLLKHKNKGKKN | 5.440 | 0.766 | 3.793 | 0.760 | 3.187 | 0.816 | 3.883 | 0.657 | 2.594 | 0.063 |
| 23 | 11. AAAHKHGHGHGKHKNKGKKN | 2.210 | 0.433 | 2.210 | 0.433 | 2.047 | 0.185 | 1.540 | 0.936 | 2.455 | 0.057 |
| 24 | 12. IIIHKHGHGHGKHKNKGKKN | 7.200 | 0.144 | 4.383 | 0.191 | 4.057 | 0.497 | 4.497 | 0.827 | 2.770 | 0.064 |
| 25 | 13. VVVHKHGHGHGKHKNKGKKN | 3.717 | 1.483 | 3.717 | 1.483 | 4.123 | 0.282 | 4.673 | 0.734 | 2.218 | 0.049 |
| 26 | 14. PPPHKHGHGHGKHKNKGKKN | 2.230 | 0.302 | 2.230 | 0.302 | 0.000 | 0.000 | 4.553 | 0.191 | 2.703 | 0.056 |
| 27 | 15. YYYHKHGHGHGKHKNKGKKN | 7.090 | 0.983 | 7.090 | 0.983 | 4.467 | 0.285 | 5.780 | 0.321 | 2.346 | 0.055 |
| 28 | 16. FHKHGHGHGKHKNKGKKN | 8.883 | 1.495 | 7.927 | 0.957 | 4.357 | 0.255 | 6.110 | 1.819 | 2.425 | 0.056 |
| 29 | 17. FFHKHGHGHGKHKNKGKKN | 4.350 | 1.419 | 2.307 | 0.811 | 3.320 | 0.314 | 3.667 | 0.552 | 2.182 | 0.052 |
| 30 | 18. FFFHKHGHGHGKHKNKGKKN | 8.307 | 1.781 | 8.877 | 0.795 | 4.140 | 0.504 | 4.543 | 0.485 | 2.303 | 0.055 |
| 31 | 19. WHKHGHGHGKHKNKGKKN | 4.253 | 1.117 | 4.253 | 1.117 | 4.090 | 1.017 | 3.950 | 0.519 | 2.503 | 0.062 |
| 32 | 20. WWHKHGHGHGKHKNKGKKN | 5.087 | 1.050 | 3.460 | 0.455 | 3.633 | 0.229 | 5.080 | 0.609 | 2.709 | 0.066 |
| 33 | 21. WWWHKHGHGHGKHKNKGKKN | 9.000 | 0.479 | 9.000 | 0.479 | 4.710 | 0.661 | 7.037 | 1.653 | 2.812 | 0.070 |
| 34 | 22. Ac-LLLHKHGHGHGKHKNKGKKN | 4.597 | 1.085 | 4.597 | 1.085 | 4.580 | 0.866 | 7.480 | 0.807 | 3.200 | 0.070 |
| 35 | 23. Ac-FFFHKHGHGHGKHKNKGKKN | 8.007 | 0.276 | 8.007 | 0.276 | 4.187 | 0.025 | 7.450 | 0.408 | 3.091 | 0.071 |
| 36 | 24. Ac-WWWHKHGHGHGKHKNKGKKN | 6.860 | 0.546 | 6.860 | 0.546 | 3.900 | 0.122 | 6.253 | 0.599 | 3.243 | 0.081 |
| 37 | 25. HKHGHGHGKHKNKGKKNWWW | 9.237 | 0.318 | 9.237 | 0.318 | 6.847 | 0.657 | 8.780 | 0.036 | 3.625 | 0.087 |
| 38 | 26. HKHGHGHGKHKNKGKKNFFF | 8.087 | 0.598 | 8.087 | 0.598 | 5.070 | 0.654 | 7.593 | 0.660 | 3.031 | 0.064 |
| 39 | 27. LLLNKKGKNHKHGHGHGHKH | 4.880 | 1.264 | 4.880 | 1.264 | 4.027 | 0.329 | 5.857 | 0.081 | 2.625 | 0.068 |
| 40 | 28. NKKGKNHKGHGHGHKHLLL | 7.943 | 0.189 | 7.943 | 0.189 | 5.957 | 0.818 | 5.663 | 0.211 | 3.261 | 0.087 |
| 41 | 29. WWWHKHGHGHGKHKNKGKK | 8.343 | 0.068 | 8.343 | 0.068 | 5.077 | 0.475 | 5.793 | 0.226 | 4.334 | 0.108 |
| 42 | 30. FFFFHKHGHGHGKHKNKGKK | 8.137 | 0.530 | 8.137 | 0.530 | 3.907 | 0.361 | 7.663 | 0.356 | 3.340 | 0.093 |
| 43 | 31. LLLLHKHGHGHGKHKNKGKK | 8.113 | 0.388 | 8.113 | 0.388 | 3.917 | 0.156 | 8.177 | 1.028 | 3.006 | 0.082 |
| 44 | 32. IIIIHKHGHGHGKHKNKGKK | 5.877 | 0.556 | 5.877 | 0.556 | 3.423 | 0.525 | 4.747 | 0.651 | 2.534 | 0.062 |
| 45 | 33. HKHGHGHGKHKNKGKKN | 2.167 | 1.016 | 2.167 | 1.016 | 0.797 | 0.200 | 1.347 | 0.516 | 2.194 | 0.051 |
| 46 | 34. HKHGHGHGKHKNKGKKNGKH | 8.483 | 1.270 | 3.257 | 0.843 | 2.183 | 0.306 | 2.340 | 0.387 | 2.376 | 0.037 |
| 47 | 35. HKHGHGHLKHKNKGKKNGKH | 3.413 | 0.083 | 3.413 | 0.083 | 2.937 | 0.067 | 3.147 | 0.344 | 2.212 | 0.052 |
| 48 | 36. HKHGHLHLKUKNKGKKNGKH | 0.000 | 0.000 | 0.000 | 0.000 | 0.000 | 0.000 | 0.000 | 0.000 | 2.194 | 0.052 |
| 49 | 37. HKHLHLHLKHKNKGKKNGKH | 8.030 | 0.114 | 8.030 | 0.114 | 4.073 | 0.548 | 5.993 | 0.178 | 3.564 | 0.069 |
| 50 | 38. HKHLHGHLKHKNKLKKNGKH | 4.967 | 1.704 | 4.967 | 1.704 | 2.807 | 0.348 | 3.800 | 0.249 | 2.334 | 0.051 |
| 51 | 39. HKHGHLHLKHKNKLKKNGKH | 6.537 | 0.408 | 4.157 | 0.100 | 2.520 | 0.236 | 3.310 | 0.489 | 2.303 | 0.051 |
| 52 | 40. HKHGHGHLKHKNKLKKNGKH | 3.577 | 0.186 | 3.577 | 0.186 | 2.720 | 0.113 | 3.237 | 0.153 | 2.425 | 0.058 |
| 53 | 41. HKHGHGHGKHKNKLKKNGKH | 6.473 | 0.575 | 3.203 | 0.309 | 3.417 | 0.375 | 2.177 | 0.170 | 2.346 | 0.053 |
| 54 | 42. GKHKNKGKKNGKHNGWK | 5.513 | 0.408 | 5.513 | 0.408 | 4.303 | 0.267 | 4.280 | 0.359 | 2.461 | 0.059 |
| 55 | 43. LGKHKNKGKKNGKHNGWK | 3.970 | 0.070 | 3.970 | 0.070 | 2.597 | 0.249 | 3.457 | 0.075 | 3.140 | 0.056 |
| 56 | 44. LLGKHKNKGKKNGKHNGWK | 7.500 | 0.384 | 7.500 | 0.384 | 3.417 | 0.107 | 4.227 | 0.227 | 3.152 | 0.081 |
| 57 | 45. LLLGKHKNKGKKNGKHNGWK | 7.237 | 0.444 | 7.237 | 0.444 | 3.653 | 0.242 | 5.200 | 0.401 | 2.667 | 0.072 |
| 58 | 46. GKHKNKGKKNGKHNGWKL | 6.077 | 0.136 | 6.077 | 0.136 | 4.390 | 0.436 | 4.420 | 0.316 | 2.564 | 0.062 |
| 59 | 47. GKHKNKGKKNGKHNGWKLL | 10.190 | 0.793 | 10.190 | 0.793 | 4.297 | 0.086 | 5.447 | 0.085 | 2.909 | 0.079 |
| 60 | 48. GKHKNKGKKNGKHNGWKLLL | 9.607 | 0.811 | 9.607 | 0.811 | 4.913 | 0.497 | 4.083 | 0.161 | 3.061 | 0.078 |
| 61 | 49. GKHKNKGKKLNGKHNGWK | 6.793 | 1.198 | 6.793 | 1.198 | 3.490 | 0.384 | 4.047 | 0.470 | 2.467 | 0.061 |
| 62 | 50. GKHKNKGKKLLNGKHNGWK | 9.500 | 1.621 | 9.500 | 1.621 | 3.700 | 0.534 | 3.970 | 0.092 | 3.237 | 0.080 |
| 63 | 51. GKHKNKGKKLLLNGKHNGWK | 6.897 | 0.075 | 6.897 | 0.075 | 3.263 | 0.312 | 4.300 | 0.176 | 2.722 | 0.068 |
| 64 | 52. AAAGKHKNKGKKNGKHNGWK | 5.380 | 1.592 | 5.380 | 1.592 | 2.757 | 0.250 | 3.353 | 0.253 | 2.661 | 0.069 |
| 65 | 53. IIIGKHKNKGKKNGKHNGWK | 6.627 | 0.293 | 6.627 | 0.293 | 3.247 | 0.189 | 4.770 | 0.690 | 2.885 | 0.081 |
| 66 | 54. FFFGKHKNKGKKNGKHNGWK | 7.530 | 0.190 | 7.530 | 0.190 | 3.910 | 0.123 | 5.847 | 0.376 | 3.352 | 0.095 |
| 67 | 55. WWWGKHKNKGKKNGKHNGWK | 9.757 | 0.179 | 9.757 | 0.179 | 4.133 | 0.575 | 7.140 | 0.391 | 2.703 | 0.068 |
| 68 | 56. GKHKNKGKKNGKHNGWK | 5.910 | 0.075 | 5.910 | 0.075 | 3.237 | 0.292 | 3.807 | 0.253 | 2.109 | 0.046 |
| 69 | 57. Ac-LLLGKHKNKGKKNGKHNGWK | 5.743 | 0.061 | 5.743 | 0.061 | 3.757 | 0.040 | 6.237 | 0.644 | 2.812 | 0.071 |
| 70 | 58. Ac-FFFGKHKNKGKKNGKHNGWK | 6.573 | 0.317 | 6.573 | 0.317 | 3.970 | 0.387 | 6.493 | 0.559 | 2.709 | 0.069 |
| 71 | 59. Ac-WWWGKHKNKGKKNGKHNGWK | 8.043 | 0.172 | 8.043 | 0.172 | 3.953 | 0.454 | 6.187 | 0.701 | 3.685 | 0.099 |
| 72 | 60. GKHKNKGKKNGKHNGWKWWW | 9.350 | 0.282 | 9.350 | 0.282 | 7.187 | 0.471 | 7.757 | 0.659 | 4.298 | 0.117 |
| 73 | 61. GKHKNKGKKNGKHNGWKFFF | 8.487 | 1.186 | 8.487 | 1.186 | 7.200 | 0.321 | 8.033 | 0.775 | 4.776 | 0.134 |
| 74 | 62. HKHGHLHLKHKNKGKKNGKH | 5.537 | 1.380 | 5.537 | 1.380 | 2.743 | 0.544 | 3.123 | 0.663 | 2.437 | 0.059 |
| 75 |  HKHGHLHLKHKNKGKKNGKH | 6.003 | 2.117 | 6.003 | 2.117 | 3.057 | 0.345 | 4.033 | 0.362 | 2.170 | 0.052 |
|  | LL-37 | 6.53 | 0.256 | 0.653 | 0.256 | 4.660 | 0.969 | 4.890 | 1.092 | 21.464 | 0.765 |

TABLE 1b

| SEQ ID No. | | sequence | RDA values (mm) | | | |
|---|---|---|---|---|---|---|
| | | | E. coli ATCC 25922 10 mM Tris Hcl (pH 7.4) | | S. aureus ATCC 29213 in 10 mM Tris Hcl (pH 7.4) | |
| 76 | T1 | KNKGKKNGKH | 2.56 | 0.33 | 0.00 | 0.00 |
| 77 | T2 | KNKGKKNGKHWWW | 8.90 | 0.47 | 4.23 | 0.78 |
| 78 | T3 | KNKGKKNGKWWW | 9.16 | 0.64 | 4.07 | 0.08 |
| 79 | T4 | KNKGKKNGWWW | nd | nd | nd | nd |
| 80 | T5 | KNKGKKNWWW | 8.36 | 0.47 | 2.85 | 0.44 |
| 81 | T6 | KNKGKKWWW | 8.16 | 0.45 | 2.79 | 0.27 |
| 82 | T7 | KNKGKWWW | 6.84 | 0.52 | 0.00 | 0.00 |
| 83 | T8 | KNKGWWW | 2.94 | 0.72 | 0.00 | 0.00 |
| 84 | T9 | KNKWWW | 2.73 | 0.10 | 0.00 | 0.00 |
| 85 | T10 | KNWWW | 2.69 | 0.95 | 0.00 | 0.00 |
| 86 | T11 | KWWW | 0.00 | 0.00 | 0.00 | 0.00 |
| 87 | T12 | WWW | 0.00 | 0.00 | 0.00 | 0.00 |
| 88 | T13 | KNKGKKNGKHWWWWW | 7.93 | 0.18 | 5.58 | 0.59 |
| 89 | T14 | KNKGKKNGKWWWWW | 7.90 | 0.83 | 5.07 | 0.24 |
| 90 | T15 | KNKGKKNGWWWWW | 8.03 | 0.04 | 3.90 | 0.52 |
| 91 | T16 | KNKGKKNWWWWW | 9.09 | 0.06 | 3.83 | 0.55 |
| 92 | T17 | KNKGKKWWWWW | 8.98 | 0.28 | 3.88 | 0.26 |
| 93 | T18 | KNKGKWWWWW | 8.21 | 0.14 | 1.82 | 0.26 |
| 94 | T19 | KNKGWWWWW | 4.49 | 0.26 | 1.10 | 0.09 |
| 95 | T20 | KNKWWWWW | 4.22 | 0.02 | 0.55 | 0.08 |
| 96 | T21 | KNWWWWW | 1.70 | 0.37 | 0.00 | 0.00 |
| 97 | T22 | KWWWWW | 2.18 | 0.27 | 0.00 | 0.00 |
| 98 | T23 | KNKGKKNGKHWWW | 8.65 | 0.18 | 3.26 | 0.27 |
| 99 | T24 | NKGKKNGKHWWW | 8.44 | 0.49 | 2.41 | 0.54 |
| 100 | T25 | KGKKNGKHWWW | 8.87 | 0.23 | 2.55 | 0.17 |
| 101 | T26 | GKKNGKHWWW | 7.47 | 0.57 | 1.76 | 0.32 |
| 102 | T27 | KKNGKHWWW | 7.56 | 0.30 | 1.68 | 0.35 |
| 103 | T28 | KNGKHWWW | 4.99 | 0.52 | 0.00 | 0.00 |
| 104 | T29 | NGKHWWW | 0.00 | 0.00 | 0.00 | 0.00 |
| 105 | T30 | GKHWWW | 3.05 | 0.01 | 0.00 | 0.00 |
| 106 | T31 | KHWWW | 1.48 | 0.21 | 0.00 | 0.00 |
| 107 | T32 | HWWW | 0.00 | 0.00 | 0.00 | 0.00 |
| 108 | T33 | WWWKNKGKKNGKH | 7.95 | 0.31 | 2.20 | 0.40 |
| 109 | T34 | WWWKNKGKKNGK | 4.94 | 0.82 | 0.43 | 0.24 |
| 110 | T35 | WWWKNKGKKNG | 1.57 | 0.08 | 0.00 | 0.00 |
| 111 | T36 | WWWKNKGKKN | 5.04 | 0.18 | 0.66 | 0.09 |
| 112 | T37 | WWWKNKGKK | 3.28 | 0.06 | 0.11 | 0.06 |

TABLE 1b-continued

| SEQ ID No. | | sequence | RDA values (mm) | | | |
|---|---|---|---|---|---|---|
| | | | *E. coli* ATCC 25922 10 mM Tris Hcl (pH 7.4) | | *S. aureus* ATCC 29213 in 10 mM Tris Hcl (pH 7.4) | |
| 113 | T38 | WWWKNKGK | 1.42 | 0.15 | 0.00 | 0.00 |
| 114 | T39 | WWWKNKG | 0.00 | 0.00 | 0.00 | 0.00 |
| 115 | T40 | WWWKNK | 0.00 | 0.00 | 0.00 | 0.00 |
| 116 | T41 | WWWKN | 0.00 | 0.00 | 0.00 | 0.00 |
| 117 | T42 | WWWK | 0.00 | 0.00 | 0.00 | 0.00 |
| 118 | T43 | SNSGSSNGSH | 0.00 | 0.00 | 0.00 | 0.00 |
| 119 | T44 | SNSGSSNGSHWWW | 0.00 | 0.00 | 0.00 | 0.00 |
| 120 | T45 | WWWSNSGSSNGSH | 0.00 | 0.00 | 0.00 | 0.00 |
| 121 | T46 | KKKKKKKKKK | 5.94 | 0.71 | 1.32 | 0.40 |
| 122 | T47 | KKKKKKKKKKWWW | 7.48 | 0.13 | 4.46 | 0.71 |
| 123 | T48 | KKKKKKKKKWWW | 9.26 | 0.30 | 7.19 | 1.30 |
| 124 | T49 | KKKKKKKKWWW | 7.90 | 0.03 | 5.48 | 1.33 |
| 125 | T50 | KKKKKKKWWW | 7.82 | 0.26 | 4.90 | 0.69 |
| 126 | T51 | KKKKKKWWW | 8.12 | 0.42 | 4.16 | 0.33 |
| 127 | T52 | KKKKKWWW | 9.01 | 0.06 | 3.43 | 0.46 |
| 128 | T53 | KKKKWWW | 8.11 | 0.44 | 2.85 | 0.33 |
| 129 | T54 | KKKWWW | 4.93 | 0.48 | 2.02 | 0.49 |
| 130 | T55 | KKWWW | 2.95 | 0.43 | 1.01 | 0.38 |
| 131 | T56 | KWWW | 4.48 | 0.28 | 0.75 | 0.18 |
| 132 | T57 | SSSSSSSSSS | 0.00 | 0.00 | 0.00 | 0.00 |
| 133 | T58 | SSSSSSSSSSWWW | 0.00 | 0.00 | 0.00 | 0.00 |
| 134 | T59 | DDDDDDDDDD | 0.00 | 0.00 | 0.00 | 0.00 |
| 135 | T60 | DDDDDDDDDDWWW | 0.00 | 0.00 | 0.00 | 0.00 |
| 136 | T61 | KNKGKKNGKHGSGSPWWW | 8.64 | 0.04 | 1.52 | 0.17 |
| | LL-37 | | 7.55 | 0.36 | 3.23 | 0.67 |

TABLE 1c

| Peptide | Peptide (μM) | Data | | | Mean | SD |
|---|---|---|---|---|---|---|
| GKR-22 | 0.1 | 0.00 | 0.00 | 0.00 | 0.00 | 0.00 |
| | 0.5 | 0.00 | 0.00 | 0.00 | 0.00 | 0.00 |
| | 1 | 0.00 | 0.00 | 0.00 | 0.00 | 0.00 |
| | 5 | 0.00 | 0.00 | 0.00 | 0.00 | 0.00 |
| | 10 | 0.00 | 0.00 | 0.00 | 0.00 | 0.00 |
| | 50 | 1.04 | 1.08 | 1.01 | 1.04 | 0.04 |
| | 100 | 3.66 | 3.31 | 2.50 | 3.16 | 0.60 |
| GKR-22-WWW | 0.1 | 0.00 | 0.00 | 0.00 | 0.00 | 0.00 |
| | 0.5 | 0.00 | 0.00 | 0.00 | 0.00 | 0.00 |
| | 1 | 0.00 | 0.00 | 0.00 | 0.00 | 0.00 |
| | 5 | 0.00 | 0.00 | 0.00 | 0.00 | 0.00 |
| | 10 | 0.50 | 0.94 | 0.54 | 0.66 | 0.24 |
| | 50 | 1.95 | 1.59 | 1.40 | 1.65 | 0.28 |
| | 100 | 5.30 | 5.74 | 5.62 | 5.55 | 0.23 |
| PKR-21 | 0.1 | 0.00 | 0.00 | 0.00 | 0.00 | 0.00 |
| | 0.5 | 0.00 | 0.00 | 0.00 | 0.00 | 0.00 |
| | 1 | 0.00 | 0.00 | 0.00 | 0.00 | 0.00 |
| | 5 | 0.00 | 0.00 | 0.00 | 0.00 | 0.00 |
| | 10 | 0.42 | 0.39 | 0.58 | 0.46 | 0.10 |
| | 50 | 4.66 | 3.95 | 3.51 | 4.04 | 0.58 |
| | 100 | 4.65 | 4.56 | 4.55 | 4.59 | 0.06 |
| PKR-21-WWW | 0.1 | 0.00 | 0.00 | 0.00 | 0.00 | 0.00 |
| | 0.5 | 0.00 | 0.00 | 0.00 | 0.00 | 0.00 |
| | 1 | 0.55 | 0.42 | 0.51 | 0.49 | 0.07 |
| | 5 | 1.26 | 1.06 | 1.10 | 1.14 | 0.11 |
| | 10 | 3.54 | 2.82 | 2.97 | 3.11 | 0.38 |
| | 50 | 5.84 | 5.44 | 5.13 | 5.47 | 0.36 |
| | 100 | 6.69 | 7.04 | 7.19 | 6.97 | 0.26 |

TABLE 1d

| Peptide | Peptide (μM) | Data | | | Mean | SD |
|---|---|---|---|---|---|---|
| GKR-22 | 0.1 | 0 | 0 | 0 | 0.00 | 0.00 |
| | 0.5 | 0 | 0 | 0 | 0.00 | 0.00 |
| | 1 | 0 | 0 | 0 | 0.00 | 0.00 |
| | 5 | 1.88 | 1.85 | 2.07 | 1.93 | 0.12 |
| | 10 | 2.07 | 3.47 | 2.74 | 2.76 | 0.70 |
| | 50 | 3.68 | 3.65 | 3.61 | 3.65 | 0.04 |
| | 100 | 4.5 | 5.24 | 4.19 | 4.64 | 0.54 |
| GKR-22-WWW | 0.1 | 0 | 0 | 0 | 0.00 | 0.00 |
| | 0.5 | 0.14 | 0.85 | 0.17 | 0.39 | 0.40 |
| | 1 | 2.74 | 3.2 | 2.59 | 2.84 | 0.32 |
| | 5 | 2.97 | 3.58 | 3.2 | 3.25 | 0.31 |
| | 10 | 5.67 | 5.68 | 5.48 | 5.61 | 0.11 |
| | 50 | 6.61 | 6.64 | 6.47 | 6.57 | 0.09 |
| | 100 | 7.8 | 8.04 | 8.12 | 7.99 | 0.17 |
| PKR-21 | 0.1 | 0 | 0 | 0 | 0.00 | 0.00 |
| | 0.5 | 0.3 | 0.7 | 0.58 | 0.53 | 0.21 |
| | 1 | 0.56 | 0.97 | 1.02 | 0.85 | 0.25 |
| | 5 | 0.63 | 1.65 | 0.55 | 0.94 | 0.61 |
| | 10 | 0.94 | 1.08 | 1.02 | 1.01 | 0.07 |
| | 50 | 1.16 | 1.52 | 1.01 | 1.23 | 0.26 |
| | 100 | 1.34 | 1.37 | 1.39 | 1.37 | 0.03 |
| PKR-21-WWW | 0.1 | 0 | 0 | 0 | 0.00 | 0.00 |
| | 0.5 | 1.26 | 1.05 | 0.84 | 1.05 | 0.21 |
| | 1 | 3.6 | 2.59 | 3.49 | 3.23 | 0.55 |
| | 5 | 4.99 | 5.03 | 4.75 | 4.92 | 0.15 |
| | 10 | 5.86 | 5.87 | 6.13 | 5.95 | 0.15 |
| | 50 | 7.71 | 7.97 | 6.98 | 7.55 | 0.51 |
| | 100 | 7.34 | 8.26 | 7.99 | 7.86 | 0.47 |

TABLE 1e

| Peptide | Peptide (μM) | Data | | | Mean | SD |
|---|---|---|---|---|---|---|
| GKR-22 | 0.1 | 0 | 0 | 0 | 0.00 | 0.00 |
| | 0.5 | 0 | 0 | 0 | 0.00 | 0.00 |
| | 1 | 0.4 | 0.26 | 0.25 | 0.30 | 0.08 |
| | 5 | 1.87 | 1.67 | 2.03 | 1.86 | 0.18 |
| | 10 | 2.37 | 2.46 | 1.95 | 2.26 | 0.27 |
| | 50 | 3.03 | 3.09 | 2.96 | 3.03 | 0.07 |
| | 100 | 3.88 | 3.94 | 3.07 | 3.63 | 0.49 |
| GKR-22-WWW | 0.1 | 0 | 0 | 0 | 0.00 | 0.00 |
| | 0.5 | 0.36 | 0.49 | 0.6 | 0.48 | 0.12 |
| | 1 | 3.6 | 3.67 | 3.78 | 3.68 | 0.09 |
| | 5 | 3.87 | 4.57 | 4.53 | 4.32 | 0.39 |
| | 10 | 6.04 | 6.87 | 5.73 | 6.21 | 0.59 |
| | 50 | 7.12 | 8.12 | 7.41 | 7.55 | 0.51 |
| | 100 | 7.4 | 8.78 | 8.05 | 8.08 | 0.69 |
| PKR-21 | 0.1 | 0 | 0 | 0 | 0.00 | 0.00 |
| | 0.5 | 0 | 0 | 0 | 0.00 | 0.00 |
| | 1 | 0 | 0 | 0 | 0.00 | 0.00 |
| | 5 | 0 | 0 | 0 | 0.00 | 0.00 |
| | 10 | 0.17 | 0.4 | 0.77 | 0.45 | 0.30 |
| | 50 | 1.06 | 1.6 | 1.24 | 1.30 | 0.27 |
| | 100 | 2.63 | 2.54 | 1.84 | 2.34 | 0.43 |
| PKR-21-WWW | 0.1 | 0 | 0 | 0 | 0.00 | 0.00 |
| | 0.5 | 0 | 0 | 0 | 0.00 | 0.00 |
| | 1 | 2.56 | 2.59 | 3.06 | 2.74 | 0.28 |
| | 5 | 2.98 | 2.5 | 3.07 | 2.85 | 0.31 |
| | 10 | 3.53 | 4.06 | 3.83 | 3.81 | 0.27 |
| | 50 | 4.21 | 5.14 | 4.23 | 4.53 | 0.53 |
| | 100 | 4.77 | 5.67 | 5.02 | 5.15 | 0.46 |

The invention claimed is:

1. An antimicrobial peptide comprising
   a) a first amino acid sequence selected from SEQ ID NOs: 13 and 54; and
   b) a second amino acid sequence consisting of 3 to 8 contiguous hydrophobic amino acid residues directly linked to the first amino acid sequence at the C-terminus, N-terminus or both, wherein the hydrophobic amino acid residues are independently selected from Y, L, I, F, Y or W.

2. The antimicrobial peptide according to claim 1, wherein said second amino acid sequence is selected from the group consisting of $F_{(3-8)}$ (SEQ ID NO: 155), $W_{(3-8)}$ (SEQ ID NO: 156), $I_{(3-8)}$ (SEQ ID NO:157), $Y_{(3-8)}$ (SEQ ID NO:158), and $V_{(3-8)}$ (SEQ ID NO:159).

3. The antimicrobial peptide according to claim 1, wherein the peptide is modified by amidation, esterification, acylation, acetylation, PEGylation, or alkylation.

4. The antimicrobial peptide according to claim 1, wherein the antimicrobial peptide is selected from the group consisting of SEQ ID NOs: 16, 19, 24, 25, 27, 30, 33-38, 41-44, 57, 60, 65-67 and 69-73.

5. An antimicrobial/pharmaceutical composition comprising
   a) an antimicrobial peptide according to claim 1 and
   b) an acceptable buffer, diluent, carrier, adjuvant or excipient.

6. The antimicrobial/pharmaceutical composition according to claim 5, comprising one or more antimicrobial peptides.

7. The antimicrobial/pharmaceutical composition according to claim 5, wherein the pharmaceutical composition comprises one or more antibiotic and/or antiseptic agent(s) and/or immunomodulating agents and/or antipruritus agents and/or steroids.

8. The antimicrobial/pharmaceutical composition according to claim 5, wherein the antimicrobial/pharmaceutical composition is in the form of granules, powders, tablets, coated tablets, coating of catheters and needles, capsules, suppositories, syrups, emulsions, gels, ointments, dispersions, suspensions, creams, aerosols, droplets or injectable forms.

9. A product comprising the antimicrobial peptide according to claim 1, wherein the product is selected from the group consisting of bandages, plasters, sutures, soap, tampons, diapers, shampoos, tooth paste, anti-acne compounds, suncreams, textiles, adhesives, incorporated in wound dressings, cleaning solutions, contact lenses, or implants.

10. A method of treating a mammal having a bacterial or fungal infection or disease, comprising administering to the mammal a therapeutically effective amount of a pharmaceutical composition according to claim 5.

* * * * *

SEQUENCE LISTING

<160> NUMBER OF SEQ ID NOS: 162

<210> SEQ ID NO 1
<211> LENGTH: 83
<212> TYPE: PRT
<213> ORGANISM: Homo sapiens

<400> SEQUENCE: 1

Lys His Asn Leu Gly His Gly His Lys His Glu Arg Asp Gln Gly His
1               5                   10                  15

Gly His Gln Arg Gly His Gly Leu Gly His Gly His Glu Gln Gln His
                20                  25                  30

Gly Leu Gly His Gly His Lys Phe Lys Leu Asp Asp Asp Leu Glu His
            35                  40                  45

Gln Gly Gly His Val Leu Asp His Gly His Lys His Lys His Gly His
    50                  55                  60

Gly His Gly Lys His Lys Asn Lys Gly Lys Lys Asn Gly Lys His Asn
65                  70                  75                  80

Gly Trp Lys

<210> SEQ ID NO 2
<211> LENGTH: 20
<212> TYPE: PRT
<213> ORGANISM: Artificial Sequence
<220> FEATURE:
<223> OTHER INFORMATION: Synthesized

<400> SEQUENCE: 2

Phe Phe Phe His Lys His Gly His Gly His Gly Lys His Lys Asn Lys
1               5                   10                  15

Gly Lys Lys Asn
            20

<210> SEQ ID NO 3
<211> LENGTH: 20
<212> TYPE: PRT
<213> ORGANISM: Artificial Sequence
<220> FEATURE:
<223> OTHER INFORMATION: Synthesized

<400> SEQUENCE: 3

Trp Trp Trp His Lys His Gly His Gly His Gly Lys His Lys Asn Lys
1               5                   10                  15

Gly Lys Lys Asn
            20

<210> SEQ ID NO 4
<211> LENGTH: 20
<212> TYPE: PRT
<213> ORGANISM: Artificial Sequence
<220> FEATURE:
<223> OTHER INFORMATION: Synthesized

<400> SEQUENCE: 4

His Lys His Gly His Gly His Gly Lys His Lys Asn Lys Gly Lys Lys
1               5                   10                  15

Asn Trp Trp Trp
            20

<210> SEQ ID NO 5
<211> LENGTH: 20
<212> TYPE: PRT
<213> ORGANISM: Artificial Sequence
<220> FEATURE:
<223> OTHER INFORMATION: Synthesized

<400> SEQUENCE: 5

His Lys His Gly His Gly His Gly Lys His Lys Asn Lys Gly Lys Lys
1               5                   10                  15

Asn Phe Phe Phe
            20

<210> SEQ ID NO 6
<211> LENGTH: 20
<212> TYPE: PRT
<213> ORGANISM: Artificial Sequence
<220> FEATURE:
<223> OTHER INFORMATION: Synthesized

<400> SEQUENCE: 6

Phe Phe Phe Gly Lys His Lys Asn Lys Gly Lys Lys Asn Gly Lys His
1               5                   10                  15

Asn Gly Trp Lys
            20

<210> SEQ ID NO 7
<211> LENGTH: 20
<212> TYPE: PRT
<213> ORGANISM: Artificial Sequence
<220> FEATURE:
<223> OTHER INFORMATION: Synthesized

<400> SEQUENCE: 7

Trp Trp Trp Gly Lys His Lys Asn Lys Gly Lys Lys Asn Gly Lys His
1               5                   10                  15

Asn Gly Trp Lys
            20

<210> SEQ ID NO 8
<211> LENGTH: 20
<212> TYPE: PRT
<213> ORGANISM: Artificial Sequence
<220> FEATURE:
<223> OTHER INFORMATION: Synthesized

<400> SEQUENCE: 8

Gly Lys His Lys Asn Lys Gly Lys Lys Asn Gly Lys His Asn Gly Trp
1               5                   10                  15

Lys Trp Trp Trp
            20

<210> SEQ ID NO 9
<211> LENGTH: 20
<212> TYPE: PRT
<213> ORGANISM: Artificial Sequence
<220> FEATURE:
<223> OTHER INFORMATION: Synthesized

<400> SEQUENCE: 9

Gly Lys His Lys Asn Lys Gly Lys Lys Asn Gly Lys His Asn Gly Trp
1               5                   10                  15

Lys Phe Phe Phe
            20

<210> SEQ ID NO 10
<211> LENGTH: 17
<212> TYPE: PRT
<213> ORGANISM: Artificial Sequence
<220> FEATURE:
<223> OTHER INFORMATION: Synthesized

<400> SEQUENCE: 10

His Lys His Gly His Gly His Gly Lys His Lys Asn Lys Gly Lys Lys
1               5                   10                  15

Asn

<210> SEQ ID NO 11
<211> LENGTH: 20
<212> TYPE: PRT
<213> ORGANISM: Artificial Sequence
<220> FEATURE:
<223> OTHER INFORMATION: Synthesized

<400> SEQUENCE: 11

His Lys His Gly His Gly His Gly Lys His Lys Asn Lys Gly Lys Lys
1               5                   10                  15

Asn Gly Lys His
            20

<210> SEQ ID NO 12
<211> LENGTH: 17
<212> TYPE: PRT
<213> ORGANISM: Artificial Sequence
<220> FEATURE:
<223> OTHER INFORMATION: Synthesized

<400> SEQUENCE: 12

Gly Lys His Lys Asn Lys Gly Lys Lys Asn Gly Lys His Asn Gly Trp
1               5                   10                  15

Lys

<210> SEQ ID NO 13
<211> LENGTH: 17
<212> TYPE: PRT
<213> ORGANISM: Artificial Sequence
<220> FEATURE:
<223> OTHER INFORMATION: Synthesized

<400> SEQUENCE: 13

His Lys His Gly His Gly His Gly Lys His Lys Asn Lys Gly Lys Lys
1               5                   10                  15
Asn

<210> SEQ ID NO 14
<211> LENGTH: 18
<212> TYPE: PRT
<213> ORGANISM: Artificial Sequence
<220> FEATURE:
<223> OTHER INFORMATION: Synthesized

<400> SEQUENCE: 14

Leu His Lys His Gly His Gly His Gly Lys His Lys Asn Lys Gly Lys
1               5                   10                  15
Lys Asn

<210> SEQ ID NO 15
<211> LENGTH: 19
<212> TYPE: PRT
<213> ORGANISM: Artificial Sequence
<220> FEATURE:
<223> OTHER INFORMATION: Synthesized

<400> SEQUENCE: 15

Leu Leu His Lys His Gly His Gly His Gly Lys His Lys Asn Lys Gly
1               5                   10                  15
Lys Lys Asn

<210> SEQ ID NO 16
<211> LENGTH: 20
<212> TYPE: PRT
<213> ORGANISM: Artificial Sequence
<220> FEATURE:
<223> OTHER INFORMATION: Synthesized

<400> SEQUENCE: 16

Leu Leu Leu His Lys His Gly His Gly His Gly Lys His Lys Asn Lys
1               5                   10                  15
Gly Lys Lys Asn
            20

<210> SEQ ID NO 17
<211> LENGTH: 18
<212> TYPE: PRT
<213> ORGANISM: Artificial Sequence
<220> FEATURE:
<223> OTHER INFORMATION: Synthesized

<400> SEQUENCE: 17

His Lys His Gly His Gly His Gly Lys His Lys Asn Lys Gly Lys Lys
1               5                   10                  15
Asn Leu

<210> SEQ ID NO 18
<211> LENGTH: 19
<212> TYPE: PRT
<213> ORGANISM: Artificial Sequence

```
<220> FEATURE:
<223> OTHER INFORMATION: Synthesized

<400> SEQUENCE: 18

His Lys His Gly His Gly His Gly Lys His Lys Asn Lys Gly Lys Lys
1               5                   10                  15

Asn Leu Leu

<210> SEQ ID NO 19
<211> LENGTH: 20
<212> TYPE: PRT
<213> ORGANISM: Artificial Sequence
<220> FEATURE:
<223> OTHER INFORMATION: Synthesized

<400> SEQUENCE: 19

His Lys His Gly His Gly His Gly Lys His Lys Asn Lys Gly Lys Lys
1               5                   10                  15

Asn Leu Leu Leu
            20

<210> SEQ ID NO 20
<211> LENGTH: 18
<212> TYPE: PRT
<213> ORGANISM: Artificial Sequence
<220> FEATURE:
<223> OTHER INFORMATION: Synthesized

<400> SEQUENCE: 20

His Lys His Gly His Gly His Gly Leu Lys His Lys Asn Lys Gly Lys
1               5                   10                  15

Lys Asn

<210> SEQ ID NO 21
<211> LENGTH: 19
<212> TYPE: PRT
<213> ORGANISM: Artificial Sequence
<220> FEATURE:
<223> OTHER INFORMATION: Synthesized

<400> SEQUENCE: 21

His Lys His Gly His Gly His Gly Leu Leu Lys His Lys Asn Lys Gly
1               5                   10                  15

Lys Lys Asn

<210> SEQ ID NO 22
<211> LENGTH: 20
<212> TYPE: PRT
<213> ORGANISM: Artificial Sequence
<220> FEATURE:
<223> OTHER INFORMATION: Synthesized

<400> SEQUENCE: 22

His Lys His Gly His Gly His Gly Leu Leu Leu Lys His Lys Asn Lys
1               5                   10                  15

Gly Lys Lys Asn
            20

<210> SEQ ID NO 23
<211> LENGTH: 20
<212> TYPE: PRT
<213> ORGANISM: Artificial Sequence
<220> FEATURE:
<223> OTHER INFORMATION: Synthesized
```

```
<400> SEQUENCE: 23

Ala Ala Ala His Lys His Gly His Gly His Gly Lys His Lys Asn Lys
1               5                   10                  15

Gly Lys Lys Asn
            20

<210> SEQ ID NO 24
<211> LENGTH: 20
<212> TYPE: PRT
<213> ORGANISM: Artificial Sequence
<220> FEATURE:
<223> OTHER INFORMATION: Synthesized

<400> SEQUENCE: 24

Ile Ile Ile His Lys His Gly His Gly His Gly Lys His Lys Asn Lys
1               5                   10                  15

Gly Lys Lys Asn
            20

<210> SEQ ID NO 25
<211> LENGTH: 20
<212> TYPE: PRT
<213> ORGANISM: Artificial Sequence
<220> FEATURE:
<223> OTHER INFORMATION: Synthesized

<400> SEQUENCE: 25

Val Val Val His Lys His Gly His Gly His Gly Lys His Lys Asn Lys
1               5                   10                  15

Gly Lys Lys Asn
            20

<210> SEQ ID NO 26
<211> LENGTH: 20
<212> TYPE: PRT
<213> ORGANISM: Artificial Sequence
<220> FEATURE:
<223> OTHER INFORMATION: Synthesized

<400> SEQUENCE: 26

Pro Pro Pro His Lys His Gly His Gly His Gly Lys His Lys Asn Lys
1               5                   10                  15

Gly Lys Lys Asn
            20

<210> SEQ ID NO 27
<211> LENGTH: 20
<212> TYPE: PRT
<213> ORGANISM: Artificial Sequence
<220> FEATURE:
<223> OTHER INFORMATION: Synthesized

<400> SEQUENCE: 27

Tyr Tyr Tyr His Lys His Gly His Gly His Gly Lys His Lys Asn Lys
1               5                   10                  15

Gly Lys Lys Asn
            20

<210> SEQ ID NO 28
<211> LENGTH: 18
<212> TYPE: PRT
<213> ORGANISM: Artificial Sequence
<220> FEATURE:
<223> OTHER INFORMATION: Synthesized
```

<400> SEQUENCE: 28

Phe His Lys His Gly His Gly His Gly Lys His Lys Asn Lys Gly Lys
1               5                   10                  15

Lys Asn

<210> SEQ ID NO 29
<211> LENGTH: 19
<212> TYPE: PRT
<213> ORGANISM: Artificial Sequence
<220> FEATURE:
<223> OTHER INFORMATION: Synthesized

<400> SEQUENCE: 29

Phe Phe His Lys His Gly His Gly His Gly Lys His Lys Asn Lys Gly
1               5                   10                  15

Lys Lys Asn

<210> SEQ ID NO 30
<211> LENGTH: 20
<212> TYPE: PRT
<213> ORGANISM: Artificial Sequence
<220> FEATURE:
<223> OTHER INFORMATION: Synthesized

<400> SEQUENCE: 30

Phe Phe Phe His Lys His Gly His Gly His Gly Lys His Lys Asn Lys
1               5                   10                  15

Gly Lys Lys Asn
            20

<210> SEQ ID NO 31
<211> LENGTH: 18
<212> TYPE: PRT
<213> ORGANISM: Artificial Sequence
<220> FEATURE:
<223> OTHER INFORMATION: Synthesized

<400> SEQUENCE: 31

Trp His Lys His Gly His Gly His Gly Lys His Lys Asn Lys Gly Lys
1               5                   10                  15

Lys Asn

<210> SEQ ID NO 32
<211> LENGTH: 19
<212> TYPE: PRT
<213> ORGANISM: Artificial Sequence
<220> FEATURE:
<223> OTHER INFORMATION: Synthesized

<400> SEQUENCE: 32

Trp Trp His Lys His Gly His Gly His Gly Lys His Lys Asn Lys Gly
1               5                   10                  15

Lys Lys Asn

<210> SEQ ID NO 33
<211> LENGTH: 20
<212> TYPE: PRT
<213> ORGANISM: Artificial Sequence
<220> FEATURE:
<223> OTHER INFORMATION: Synthesized

<400> SEQUENCE: 33

Trp Trp Trp His Lys His Gly His Gly His Gly Lys His Lys Asn Lys
1               5                   10                  15

Gly Lys Lys Asn
        20

<210> SEQ ID NO 34
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: ACETYLATION

<400> SEQUENCE: 34

Leu Leu Leu His Lys His Gly His Gly His Gly Lys His Lys Asn Lys
1               5                   10                  15

Gly Lys Lys Asn
        20

<210> SEQ ID NO 35
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: ACETYLATION

<400> SEQUENCE: 35

Phe Phe Phe His Lys His Gly His Gly His Gly Lys His Lys Asn Lys
1               5                   10                  15

Gly Lys Lys Asn
        20

<210> SEQ ID NO 36
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: ACETYLATION

<400> SEQUENCE: 36

Trp Trp Trp His Lys His Gly His Gly His Gly Lys His Lys Asn Lys
1               5                   10                  15

Gly Lys Lys Asn
        20

<210> SEQ ID NO 37
<211> LENGTH: 20
<212> TYPE: PRT
<213> ORGANISM: Artificial Sequence
<220> FEATURE:
<223> OTHER INFORMATION: Synthesized

<400> SEQUENCE: 37

His Lys His Gly His Gly His Gly Lys His Lys Asn Lys Gly Lys Lys
1               5                   10                  15

Asn Trp Trp Trp
        20

```
<210> SEQ ID NO 38
<211> LENGTH: 20
<212> TYPE: PRT
<213> ORGANISM: Artificial Sequence
<220> FEATURE:
<223> OTHER INFORMATION: Synthesized

<400> SEQUENCE: 38

His Lys His Gly His Gly His Gly Lys His Lys Asn Lys Gly Lys Lys
1               5                   10                  15

Asn Phe Phe Phe
        20

<210> SEQ ID NO 39
<211> LENGTH: 20
<212> TYPE: PRT
<213> ORGANISM: Artificial Sequence
<220> FEATURE:
<223> OTHER INFORMATION: Synthesized

<400> SEQUENCE: 39

Leu Leu Leu Asn Lys Lys Gly Lys Asn Lys His Lys Gly His Gly His
1               5                   10                  15

Gly His Lys His
        20

<210> SEQ ID NO 40
<211> LENGTH: 20
<212> TYPE: PRT
<213> ORGANISM: Artificial Sequence
<220> FEATURE:
<223> OTHER INFORMATION: Synthesized

<400> SEQUENCE: 40

Asn Lys Lys Gly Lys Asn Lys His Lys Gly His Gly His Gly His Lys
1               5                   10                  15

His Leu Leu Leu
        20

<210> SEQ ID NO 41
<211> LENGTH: 20
<212> TYPE: PRT
<213> ORGANISM: Artificial Sequence
<220> FEATURE:
<223> OTHER INFORMATION: Synthesized

<400> SEQUENCE: 41

Trp Trp Trp Trp His Lys His Gly His Gly His Gly Lys His Lys Asn
1               5                   10                  15

Lys Gly Lys Lys
        20

<210> SEQ ID NO 42
<211> LENGTH: 20
<212> TYPE: PRT
<213> ORGANISM: Artificial Sequence
<220> FEATURE:
<223> OTHER INFORMATION: Synthesized

<400> SEQUENCE: 42

Phe Phe Phe Phe His Lys His Gly His Gly His Gly Lys His Lys Asn
1               5                   10                  15

Lys Gly Lys Lys
        20
```

<210> SEQ ID NO 43
<211> LENGTH: 20
<212> TYPE: PRT
<213> ORGANISM: Artificial Sequence
<220> FEATURE:
<223> OTHER INFORMATION: Synthesized

<400> SEQUENCE: 43

Leu Leu Leu Leu His Lys His Gly His Gly His Gly Lys His Lys Asn
1               5                   10                  15

Lys Gly Lys Lys
            20

<210> SEQ ID NO 44
<211> LENGTH: 20
<212> TYPE: PRT
<213> ORGANISM: Artificial Sequence
<220> FEATURE:
<223> OTHER INFORMATION: Synthesized

<400> SEQUENCE: 44

Ile Ile Ile Ile His Lys His Gly His Gly His Gly Lys His Lys Asn
1               5                   10                  15

Lys Gly Lys Lys
            20

<210> SEQ ID NO 45
<211> LENGTH: 17
<212> TYPE: PRT
<213> ORGANISM: Artificial Sequence
<220> FEATURE:
<223> OTHER INFORMATION: Synthesized

<400> SEQUENCE: 45

His Lys His Gly His Gly His Gly Lys His Lys Asn Lys Gly Lys Lys
1               5                   10                  15

Asn

<210> SEQ ID NO 46
<211> LENGTH: 20
<212> TYPE: PRT
<213> ORGANISM: Artificial Sequence
<220> FEATURE:
<223> OTHER INFORMATION: Synthesized

<400> SEQUENCE: 46

His Lys His Gly His Gly His Gly Lys His Lys Asn Lys Gly Lys Lys
1               5                   10                  15

Asn Gly Lys His
            20

<210> SEQ ID NO 47
<211> LENGTH: 20
<212> TYPE: PRT
<213> ORGANISM: Artificial Sequence
<220> FEATURE:
<223> OTHER INFORMATION: Synthesized

<400> SEQUENCE: 47

His Lys His Gly His Gly His Leu Lys His Lys Asn Lys Gly Lys Lys
1               5                   10                  15

Asn Gly Lys His
            20

```
<210> SEQ ID NO 48
<211> LENGTH: 20
<212> TYPE: PRT
<213> ORGANISM: Artificial Sequence
<220> FEATURE:
<223> OTHER INFORMATION: Synthesized

<400> SEQUENCE: 48

His Lys His Gly His Leu His Leu Lys His Lys Asn Lys Gly Lys Lys
1               5                   10                  15

Asn Gly Lys His
            20

<210> SEQ ID NO 49
<211> LENGTH: 20
<212> TYPE: PRT
<213> ORGANISM: Artificial Sequence
<220> FEATURE:
<223> OTHER INFORMATION: Synthesized

<400> SEQUENCE: 49

His Lys His Leu His Leu His Leu Lys His Lys Asn Lys Gly Lys Lys
1               5                   10                  15

Asn Gly Lys His
            20

<210> SEQ ID NO 50
<211> LENGTH: 20
<212> TYPE: PRT
<213> ORGANISM: Artificial Sequence
<220> FEATURE:
<223> OTHER INFORMATION: Synthesized

<400> SEQUENCE: 50

His Lys His Leu His Gly His Leu Lys His Lys Asn Lys Leu Lys Lys
1               5                   10                  15

Asn Gly Lys His
            20

<210> SEQ ID NO 51
<211> LENGTH: 20
<212> TYPE: PRT
<213> ORGANISM: Artificial Sequence
<220> FEATURE:
<223> OTHER INFORMATION: Synthesized

<400> SEQUENCE: 51

His Lys His Gly His Leu His Leu Lys His Lys Asn Lys Leu Lys Lys
1               5                   10                  15

Asn Gly Lys His
            20

<210> SEQ ID NO 52
<211> LENGTH: 20
<212> TYPE: PRT
<213> ORGANISM: Artificial Sequence
<220> FEATURE:
<223> OTHER INFORMATION: Synthesized

<400> SEQUENCE: 52

His Lys His Gly His Gly His Leu Lys His Lys Asn Lys Leu Lys Lys
1               5                   10                  15

Asn Gly Lys His
            20
```

<210> SEQ ID NO 53
<211> LENGTH: 20
<212> TYPE: PRT
<213> ORGANISM: Artificial Sequence
<220> FEATURE:
<223> OTHER INFORMATION: Synthesized

<400> SEQUENCE: 53

His Lys His Gly His Gly His Gly Lys His Lys Asn Lys Leu Lys Lys
1               5                   10                  15

Asn Gly Lys His
            20

<210> SEQ ID NO 54
<211> LENGTH: 17
<212> TYPE: PRT
<213> ORGANISM: Artificial Sequence
<220> FEATURE:
<223> OTHER INFORMATION: Synthesized

<400> SEQUENCE: 54

Gly Lys His Lys Asn Lys Gly Lys Lys Asn Gly Lys His Asn Gly Trp
1               5                   10                  15

Lys

<210> SEQ ID NO 55
<211> LENGTH: 18
<212> TYPE: PRT
<213> ORGANISM: Artificial Sequence
<220> FEATURE:
<223> OTHER INFORMATION: Synthesized

<400> SEQUENCE: 55

Leu Gly Lys His Lys Asn Lys Gly Lys Lys Asn Gly Lys His Asn Gly
1               5                   10                  15

Trp Lys

<210> SEQ ID NO 56
<211> LENGTH: 19
<212> TYPE: PRT
<213> ORGANISM: Artificial Sequence
<220> FEATURE:
<223> OTHER INFORMATION: Synthesized

<400> SEQUENCE: 56

Leu Leu Gly Lys His Lys Asn Lys Gly Lys Lys Asn Gly Lys His Asn
1               5                   10                  15

Gly Trp Lys

<210> SEQ ID NO 57
<211> LENGTH: 20
<212> TYPE: PRT
<213> ORGANISM: Artificial Sequence
<220> FEATURE:
<223> OTHER INFORMATION: Synthesized

<400> SEQUENCE: 57

Leu Leu Leu Gly Lys His Lys Asn Lys Gly Lys Lys Asn Gly Lys His
1               5                   10                  15

Asn Gly Trp Lys
            20

<210> SEQ ID NO 58
<211> LENGTH: 18
<212> TYPE: PRT

<213> ORGANISM: Artificial Sequence
<220> FEATURE:
<223> OTHER INFORMATION: Synthesized

<400> SEQUENCE: 58

Gly Lys His Lys Asn Lys Gly Lys Asn Gly Lys His Asn Gly Trp
1               5                   10                  15

Lys Leu

<210> SEQ ID NO 59
<211> LENGTH: 19
<212> TYPE: PRT
<213> ORGANISM: Artificial Sequence
<220> FEATURE:
<223> OTHER INFORMATION: Synthesized

<400> SEQUENCE: 59

Gly Lys His Lys Asn Lys Gly Lys Asn Gly Lys His Asn Gly Trp
1               5                   10                  15

Lys Leu Leu

<210> SEQ ID NO 60
<211> LENGTH: 20
<212> TYPE: PRT
<213> ORGANISM: Artificial Sequence
<220> FEATURE:
<223> OTHER INFORMATION: Synthesized

<400> SEQUENCE: 60

Gly Lys His Lys Asn Lys Gly Lys Asn Gly Lys His Asn Gly Trp
1               5                   10                  15

Lys Leu Leu Leu
            20

<210> SEQ ID NO 61
<211> LENGTH: 18
<212> TYPE: PRT
<213> ORGANISM: Artificial Sequence
<220> FEATURE:
<223> OTHER INFORMATION: Synthesized

<400> SEQUENCE: 61

Gly Lys His Lys Asn Lys Gly Lys Lys Leu Asn Gly Lys His Asn Gly
1               5                   10                  15

Trp Lys

<210> SEQ ID NO 62
<211> LENGTH: 19
<212> TYPE: PRT
<213> ORGANISM: Artificial Sequence
<220> FEATURE:
<223> OTHER INFORMATION: Synthesized

<400> SEQUENCE: 62

Gly Lys His Lys Asn Lys Gly Lys Lys Leu Leu Asn Gly Lys His Asn
1               5                   10                  15

Gly Trp Lys

<210> SEQ ID NO 63
<211> LENGTH: 20
<212> TYPE: PRT
<213> ORGANISM: Artificial Sequence
<220> FEATURE:
<223> OTHER INFORMATION: Synthesized

<400> SEQUENCE: 63

Gly Lys His Lys Asn Lys Gly Lys Lys Leu Leu Leu Asn Gly Lys His
1               5                   10                  15

Asn Gly Trp Lys
            20

<210> SEQ ID NO 64
<211> LENGTH: 20
<212> TYPE: PRT
<213> ORGANISM: Artificial Sequence
<220> FEATURE:
<223> OTHER INFORMATION: Synthesized

<400> SEQUENCE: 64

Ala Ala Ala Gly Lys His Lys Asn Lys Gly Lys Lys Asn Gly Lys His
1               5                   10                  15

Asn Gly Trp Lys
            20

<210> SEQ ID NO 65
<211> LENGTH: 20
<212> TYPE: PRT
<213> ORGANISM: Artificial Sequence
<220> FEATURE:
<223> OTHER INFORMATION: Synthesized

<400> SEQUENCE: 65

Ile Ile Ile Gly Lys His Lys Asn Lys Gly Lys Lys Asn Gly Lys His
1               5                   10                  15

Asn Gly Trp Lys
            20

<210> SEQ ID NO 66
<211> LENGTH: 20
<212> TYPE: PRT
<213> ORGANISM: Artificial Sequence
<220> FEATURE:
<223> OTHER INFORMATION: Synthesized

<400> SEQUENCE: 66

Phe Phe Phe Gly Lys His Lys Asn Lys Gly Lys Lys Asn Gly Lys His
1               5                   10                  15

Asn Gly Trp Lys
            20

<210> SEQ ID NO 67
<211> LENGTH: 20
<212> TYPE: PRT
<213> ORGANISM: Artificial Sequence
<220> FEATURE:
<223> OTHER INFORMATION: Synthesized

<400> SEQUENCE: 67

Trp Trp Trp Gly Lys His Lys Asn Lys Gly Lys Lys Asn Gly Lys His
1               5                   10                  15

Asn Gly Trp Lys
            20

<210> SEQ ID NO 68
<211> LENGTH: 17
<212> TYPE: PRT
<213> ORGANISM: Artificial Sequence
<220> FEATURE:
<223> OTHER INFORMATION: Synthesized

<400> SEQUENCE: 68

Gly Lys His Lys Asn Lys Gly Lys Lys Asn Gly Lys His Asn Gly Trp
1               5                   10                  15

Lys

<210> SEQ ID NO 69
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: ACETYLATION

<400> SEQUENCE: 69

Leu Leu Leu Gly Lys His Lys Asn Lys Gly Lys Lys Asn Gly Lys His
1               5                   10                  15

Asn Gly Trp Lys
            20

<210> SEQ ID NO 70
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: ACETYLATION

<400> SEQUENCE: 70

Phe Phe Phe Gly Lys His Lys Asn Lys Gly Lys Lys Asn Gly Lys His
1               5                   10                  15

Asn Gly Trp Lys
            20

<210> SEQ ID NO 71
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: ACETYLATION

<400> SEQUENCE: 71

Trp Trp Trp Gly Lys His Lys Asn Lys Gly Lys Lys Asn Gly Lys His
1               5                   10                  15

Asn Gly Trp Lys
            20

<210> SEQ ID NO 72
<211> LENGTH: 20
<212> TYPE: PRT
<213> ORGANISM: Artificial Sequence
<220> FEATURE:
<223> OTHER INFORMATION: Synthesized

<400> SEQUENCE: 72

Gly Lys His Lys Asn Lys Gly Lys Lys Asn Gly Lys His Asn Gly Trp
1               5                   10                  15

```
<210> SEQ ID NO 73
<211> LENGTH: 20
<212> TYPE: PRT
<213> ORGANISM: Artificial Sequence
<220> FEATURE:
<223> OTHER INFORMATION: Synthesized

<400> SEQUENCE: 73

Gly Lys His Lys Asn Lys Gly Lys Lys Asn Gly Lys His Asn Gly Trp
1               5                   10                  15

Lys Phe Phe Phe
            20

<210> SEQ ID NO 74
<211> LENGTH: 20
<212> TYPE: PRT
<213> ORGANISM: Artificial Sequence
<220> FEATURE:
<223> OTHER INFORMATION: Synthesized

<400> SEQUENCE: 74

His Lys His Gly His Leu His Leu Lys His Lys Asn Lys Gly Lys Lys
1               5                   10                  15

Asn Gly Lys His
            20

<210> SEQ ID NO 75
<211> LENGTH: 20
<212> TYPE: PRT
<213> ORGANISM: Artificial Sequence
<220> FEATURE:
<223> OTHER INFORMATION: Synthesized

<400> SEQUENCE: 75

His Lys His Gly His Leu His Leu Lys His Lys Asn Lys Gly Lys Lys
1               5                   10                  15

Asn Gly Lys His
            20

<210> SEQ ID NO 76
<211> LENGTH: 10
<212> TYPE: PRT
<213> ORGANISM: Artificial Sequence
<220> FEATURE:
<223> OTHER INFORMATION: Synthesized

<400> SEQUENCE: 76

Lys Asn Lys Gly Lys Lys Asn Gly Lys His
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthesized

<400> SEQUENCE: 77

Lys Asn Lys Gly Lys Lys Asn Gly Lys His Trp Trp Trp
1               5                   10

<210> SEQ ID NO 78
<211> LENGTH: 12
```

```
<212> TYPE: PRT
<213> ORGANISM: Artificial Sequence
<220> FEATURE:
<223> OTHER INFORMATION: Synthesized

<400> SEQUENCE: 78

Lys Asn Lys Gly Lys Lys Asn Gly Lys Trp Trp Trp
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthesized

<400> SEQUENCE: 79

Lys Asn Lys Gly Lys Lys Asn Gly Trp Trp Trp
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthesized

<400> SEQUENCE: 80

Lys Asn Lys Gly Lys Lys Asn Trp Trp Trp
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Synthesized

<400> SEQUENCE: 81

Lys Asn Lys Gly Lys Lys Trp Trp Trp
1               5

<210> SEQ ID NO 82
<211> LENGTH: 8
<212> TYPE: PRT
<213> ORGANISM: Artificial Sequence
<220> FEATURE:
<223> OTHER INFORMATION: Synthesized

<400> SEQUENCE: 82

Lys Asn Lys Gly Lys Trp Trp Trp
1               5

<210> SEQ ID NO 83
<211> LENGTH: 7
<212> TYPE: PRT
<213> ORGANISM: Artificial Sequence
<220> FEATURE:
<223> OTHER INFORMATION: Synthesized

<400> SEQUENCE: 83

Lys Asn Lys Gly Trp Trp Trp
1               5

<210> SEQ ID NO 84
<211> LENGTH: 6
<212> TYPE: PRT
<213> ORGANISM: Artificial Sequence
```

<220> FEATURE:
<223> OTHER INFORMATION: Synthesized

<400> SEQUENCE: 84

Lys Asn Lys Trp Trp Trp
1               5

<210> SEQ ID NO 85
<211> LENGTH: 5
<212> TYPE: PRT
<213> ORGANISM: Artificial Sequence
<220> FEATURE:
<223> OTHER INFORMATION: Synthesized

<400> SEQUENCE: 85

Lys Asn Trp Trp Trp
1               5

<210> SEQ ID NO 86
<211> LENGTH: 4
<212> TYPE: PRT
<213> ORGANISM: Artificial Sequence
<220> FEATURE:
<223> OTHER INFORMATION: Synthesized

<400> SEQUENCE: 86

Lys Trp Trp Trp
1

<210> SEQ ID NO 87
<211> LENGTH: 3
<212> TYPE: PRT
<213> ORGANISM: Artificial Sequence
<220> FEATURE:
<223> OTHER INFORMATION: Synthesized

<400> SEQUENCE: 87

Trp Trp Trp
1

<210> SEQ ID NO 88
<211> LENGTH: 15
<212> TYPE: PRT
<213> ORGANISM: Artificial Sequence
<220> FEATURE:
<223> OTHER INFORMATION: Synthesized

<400> SEQUENCE: 88

Lys Asn Lys Gly Lys Lys Asn Gly Lys His Trp Trp Trp Trp Trp
1               5                   10                  15

<210> SEQ ID NO 89
<211> LENGTH: 14
<212> TYPE: PRT
<213> ORGANISM: Artificial Sequence
<220> FEATURE:
<223> OTHER INFORMATION: Synthesized

<400> SEQUENCE: 89

Lys Asn Lys Gly Lys Lys Asn Gly Lys Trp Trp Trp Trp Trp
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Synthesized

```
<400> SEQUENCE: 90

Lys Asn Lys Gly Lys Asn Gly Trp Trp Trp Trp Trp
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthesized

<400> SEQUENCE: 91

Lys Asn Lys Gly Lys Lys Asn Trp Trp Trp Trp Trp
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthesized

<400> SEQUENCE: 92

Lys Asn Lys Gly Lys Lys Trp Trp Trp Trp Trp
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthesized

<400> SEQUENCE: 93

Lys Asn Lys Gly Lys Trp Trp Trp Trp Trp
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Synthesized

<400> SEQUENCE: 94

Lys Asn Lys Gly Trp Trp Trp Trp Trp
1               5

<210> SEQ ID NO 95
<211> LENGTH: 8
<212> TYPE: PRT
<213> ORGANISM: Artificial Sequence
<220> FEATURE:
<223> OTHER INFORMATION: Synthesized

<400> SEQUENCE: 95

Lys Asn Lys Trp Trp Trp Trp Trp
1               5

<210> SEQ ID NO 96
<211> LENGTH: 7
<212> TYPE: PRT
<213> ORGANISM: Artificial Sequence
<220> FEATURE:
<223> OTHER INFORMATION: Synthesized

<400> SEQUENCE: 96
```

Lys Asn Trp Trp Trp Trp Trp
1               5

<210> SEQ ID NO 97
<211> LENGTH: 6
<212> TYPE: PRT
<213> ORGANISM: Artificial Sequence
<220> FEATURE:
<223> OTHER INFORMATION: Synthesized

<400> SEQUENCE: 97

Lys Trp Trp Trp Trp Trp
1               5

<210> SEQ ID NO 98
<211> LENGTH: 13
<212> TYPE: PRT
<213> ORGANISM: Artificial Sequence
<220> FEATURE:
<223> OTHER INFORMATION: Synthesized

<400> SEQUENCE: 98

Lys Asn Lys Gly Lys Lys Asn Gly Lys His Trp Trp Trp
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthesized

<400> SEQUENCE: 99

Asn Lys Gly Lys Lys Asn Gly Lys His Trp Trp Trp
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthesized

<400> SEQUENCE: 100

Lys Gly Lys Lys Asn Gly Lys His Trp Trp Trp
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthesized

<400> SEQUENCE: 101

Gly Lys Lys Asn Gly Lys His Trp Trp Trp
1               5                   10

<210> SEQ ID NO 102
<211> LENGTH: 9
<212> TYPE: PRT
<213> ORGANISM: Artificial Sequence
<220> FEATURE:
<223> OTHER INFORMATION: Synthesized

<400> SEQUENCE: 102

Lys Lys Asn Gly Lys His Trp Trp Trp

```
<210> SEQ ID NO 103
<211> LENGTH: 8
<212> TYPE: PRT
<213> ORGANISM: Artificial Sequence
<220> FEATURE:
<223> OTHER INFORMATION: Synthesized

<400> SEQUENCE: 103

Lys Asn Gly Lys His Trp Trp Trp
1               5

<210> SEQ ID NO 104
<211> LENGTH: 7
<212> TYPE: PRT
<213> ORGANISM: Artificial Sequence
<220> FEATURE:
<223> OTHER INFORMATION: Synthesized

<400> SEQUENCE: 104

Asn Gly Lys His Trp Trp Trp
1               5

<210> SEQ ID NO 105
<211> LENGTH: 6
<212> TYPE: PRT
<213> ORGANISM: Artificial Sequence
<220> FEATURE:
<223> OTHER INFORMATION: Synthesized

<400> SEQUENCE: 105

Gly Lys His Trp Trp Trp
1               5

<210> SEQ ID NO 106
<211> LENGTH: 5
<212> TYPE: PRT
<213> ORGANISM: Artificial Sequence
<220> FEATURE:
<223> OTHER INFORMATION: Synthesized

<400> SEQUENCE: 106

Lys His Trp Trp Trp
1               5

<210> SEQ ID NO 107
<211> LENGTH: 4
<212> TYPE: PRT
<213> ORGANISM: Artificial Sequence
<220> FEATURE:
<223> OTHER INFORMATION: Synthesized

<400> SEQUENCE: 107

His Trp Trp Trp
1

<210> SEQ ID NO 108
<211> LENGTH: 13
<212> TYPE: PRT
<213> ORGANISM: Artificial Sequence
<220> FEATURE:
<223> OTHER INFORMATION: Synthesized

<400> SEQUENCE: 108

Trp Trp Trp Lys Asn Lys Gly Lys Lys Asn Gly Lys His
1               5                   10
```

<210> SEQ ID NO 109
<211> LENGTH: 12
<212> TYPE: PRT
<213> ORGANISM: Artificial Sequence
<220> FEATURE:
<223> OTHER INFORMATION: Synthesized

<400> SEQUENCE: 109

Trp Trp Trp Lys Asn Lys Gly Lys Lys Asn Gly Lys
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthesized

<400> SEQUENCE: 110

Trp Trp Trp Lys Asn Lys Gly Lys Lys Asn Gly
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthesized

<400> SEQUENCE: 111

Trp Trp Trp Lys Asn Lys Gly Lys Lys Asn
1               5                   10

<210> SEQ ID NO 112
<211> LENGTH: 9
<212> TYPE: PRT
<213> ORGANISM: Artificial Sequence
<220> FEATURE:
<223> OTHER INFORMATION: Synthesized

<400> SEQUENCE: 112

Trp Trp Trp Lys Asn Lys Gly Lys Lys
1               5

<210> SEQ ID NO 113
<211> LENGTH: 8
<212> TYPE: PRT
<213> ORGANISM: Artificial Sequence
<220> FEATURE:
<223> OTHER INFORMATION: Synthesized

<400> SEQUENCE: 113

Trp Trp Trp Lys Asn Lys Gly Lys
1               5

<210> SEQ ID NO 114
<211> LENGTH: 7
<212> TYPE: PRT
<213> ORGANISM: Artificial Sequence
<220> FEATURE:
<223> OTHER INFORMATION: Synthesized

<400> SEQUENCE: 114

Trp Trp Trp Lys Asn Lys Gly
1               5

<210> SEQ ID NO 115

```
<211> LENGTH: 6
<212> TYPE: PRT
<213> ORGANISM: Artificial Sequence
<220> FEATURE:
<223> OTHER INFORMATION: Synthesized

<400> SEQUENCE: 115

Trp Trp Trp Lys Asn Lys
1               5

<210> SEQ ID NO 116
<211> LENGTH: 5
<212> TYPE: PRT
<213> ORGANISM: Artificial Sequence
<220> FEATURE:
<223> OTHER INFORMATION: Synthesized

<400> SEQUENCE: 116

Trp Trp Trp Lys Asn
1               5

<210> SEQ ID NO 117
<211> LENGTH: 4
<212> TYPE: PRT
<213> ORGANISM: Artificial Sequence
<220> FEATURE:
<223> OTHER INFORMATION: Synthesized

<400> SEQUENCE: 117

Trp Trp Trp Lys
1

<210> SEQ ID NO 118
<211> LENGTH: 10
<212> TYPE: PRT
<213> ORGANISM: Artificial Sequence
<220> FEATURE:
<223> OTHER INFORMATION: Synthesized

<400> SEQUENCE: 118

Ser Asn Ser Gly Ser Ser Asn Gly Ser His
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Synthesized

<400> SEQUENCE: 119

Ser Asn Ser Gly Ser Ser Asn Gly Ser His Trp Trp Trp
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Synthesized

<400> SEQUENCE: 120

Trp Trp Trp Ser Asn Ser Gly Ser Ser Asn Gly Ser His
1               5                   10

<210> SEQ ID NO 121
<211> LENGTH: 10
<212> TYPE: PRT
```

<213> ORGANISM: Artificial Sequence
<220> FEATURE:
<223> OTHER INFORMATION: Synthesized

<400> SEQUENCE: 121

Lys Lys Lys Lys Lys Lys Lys Lys Lys Lys
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Synthesized

<400> SEQUENCE: 122

Lys Lys Lys Lys Lys Lys Lys Lys Lys Lys Trp Trp Trp
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthesized

<400> SEQUENCE: 123

Lys Lys Lys Lys Lys Lys Lys Lys Lys Trp Trp Trp
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthesized

<400> SEQUENCE: 124

Lys Lys Lys Lys Lys Lys Lys Lys Trp Trp Trp
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Synthesized

<400> SEQUENCE: 125

Lys Lys Lys Lys Lys Lys Lys Trp Trp Trp
1               5                   10

<210> SEQ ID NO 126
<211> LENGTH: 9
<212> TYPE: PRT
<213> ORGANISM: Artificial Sequence
<220> FEATURE:
<223> OTHER INFORMATION: Synthesized

<400> SEQUENCE: 126

Lys Lys Lys Lys Lys Lys Trp Trp Trp
1               5

<210> SEQ ID NO 127
<211> LENGTH: 8
<212> TYPE: PRT
<213> ORGANISM: Artificial Sequence
<220> FEATURE:

<223> OTHER INFORMATION: Synthesized

<400> SEQUENCE: 127

Lys Lys Lys Lys Lys Trp Trp Trp
1               5

<210> SEQ ID NO 128
<211> LENGTH: 7
<212> TYPE: PRT
<213> ORGANISM: Artificial Sequence
<220> FEATURE:
<223> OTHER INFORMATION: Synthesized

<400> SEQUENCE: 128

Lys Lys Lys Lys Trp Trp Trp
1               5

<210> SEQ ID NO 129
<211> LENGTH: 6
<212> TYPE: PRT
<213> ORGANISM: Artificial Sequence
<220> FEATURE:
<223> OTHER INFORMATION: Synthesized

<400> SEQUENCE: 129

Lys Lys Lys Trp Trp Trp
1               5

<210> SEQ ID NO 130
<211> LENGTH: 5
<212> TYPE: PRT
<213> ORGANISM: Artificial Sequence
<220> FEATURE:
<223> OTHER INFORMATION: Synthesized

<400> SEQUENCE: 130

Lys Lys Trp Trp Trp
1               5

<210> SEQ ID NO 131
<211> LENGTH: 4
<212> TYPE: PRT
<213> ORGANISM: Artificial Sequence
<220> FEATURE:
<223> OTHER INFORMATION: Synthesized

<400> SEQUENCE: 131

Lys Trp Trp Trp
1

<210> SEQ ID NO 132
<211> LENGTH: 10
<212> TYPE: PRT
<213> ORGANISM: Artificial Sequence
<220> FEATURE:
<223> OTHER INFORMATION: Synthesized

<400> SEQUENCE: 132

Ser Ser Ser Ser Ser Ser Ser Ser Ser Ser
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Synthesized

```
<400> SEQUENCE: 133

Ser Ser Ser Ser Ser Ser Ser Ser Ser Trp Trp Trp
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthesized

<400> SEQUENCE: 134

Asp Asp Asp Asp Asp Asp Asp Asp Asp Asp
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Synthesized

<400> SEQUENCE: 135

Asp Asp Asp Asp Asp Asp Asp Asp Asp Asp Trp Trp Trp
1               5                   10

<210> SEQ ID NO 136
<211> LENGTH: 18
<212> TYPE: PRT
<213> ORGANISM: Artificial Sequence
<220> FEATURE:
<223> OTHER INFORMATION: Synthesized

<400> SEQUENCE: 136

Lys Asn Lys Gly Lys Lys Asn Gly Lys His Gly Ser Gly Ser Pro Trp
1               5                   10                  15

Trp Trp

<210> SEQ ID NO 137
<211> LENGTH: 20
<212> TYPE: PRT
<213> ORGANISM: Homo sapiens

<400> SEQUENCE: 137

Cys Asn Tyr Ile Thr Glu Leu Arg Arg Gln His Ala Arg Ala Ser His
1               5                   10                  15

Leu Gly Leu Ala
            20

<210> SEQ ID NO 138
<211> LENGTH: 23
<212> TYPE: PRT
<213> ORGANISM: Artificial Sequence
<220> FEATURE:
<223> OTHER INFORMATION: Synthesized

<400> SEQUENCE: 138

Cys Asn Tyr Ile Thr Glu Leu Arg Arg Gln His Ala Arg Ala Ser His
1               5                   10                  15

Leu Gly Leu Ala Trp Trp Trp
            20

<210> SEQ ID NO 139
<211> LENGTH: 20
<212> TYPE: PRT
```

-continued

<213> ORGANISM: Homo sapiens

<400> SEQUENCE: 139

Cys Lys Tyr Ile Leu Leu Leu Arg Arg Gln His Ala Arg Ala Trp Arg
1               5                   10                  15

Arg Gly Leu Arg
            20

<210> SEQ ID NO 140
<211> LENGTH: 23
<212> TYPE: PRT
<213> ORGANISM: Artificial Sequence
<220> FEATURE:
<223> OTHER INFORMATION: Synthesized

<400> SEQUENCE: 140

Cys Lys Tyr Ile Leu Leu Leu Arg Arg Gln His Ala Arg Ala Trp Arg
1               5                   10                  15

Arg Gly Leu Arg Trp Trp Trp
            20

<210> SEQ ID NO 141
<211> LENGTH: 22
<212> TYPE: PRT
<213> ORGANISM: Homo sapiens

<400> SEQUENCE: 141

Gly Lys Arg Lys Lys Lys Gly Lys Gly Leu Gly Lys Lys Arg Asp Pro
1               5                   10                  15

Cys Leu Arg Lys Tyr Lys
            20

<210> SEQ ID NO 142
<211> LENGTH: 25
<212> TYPE: PRT
<213> ORGANISM: Artificial Sequence
<220> FEATURE:
<223> OTHER INFORMATION: Synthesized

<400> SEQUENCE: 142

Gly Lys Arg Lys Lys Lys Gly Lys Gly Leu Gly Lys Lys Arg Asp Pro
1               5                   10                  15

Cys Leu Arg Lys Tyr Lys Trp Trp Trp
            20                  25

<210> SEQ ID NO 143
<211> LENGTH: 21
<212> TYPE: PRT
<213> ORGANISM: Homo sapiens

<400> SEQUENCE: 143

Pro Lys Arg Lys Lys Lys Gly Gly Lys Asn Gly Lys Asn Arg Arg Asn
1               5                   10                  15

Arg Lys Lys Lys Asn
            20

<210> SEQ ID NO 144
<211> LENGTH: 24
<212> TYPE: PRT
<213> ORGANISM: Artificial Sequence
<220> FEATURE:
<223> OTHER INFORMATION: Synthesized

<400> SEQUENCE: 144

Pro Lys Arg Lys Lys Gly Gly Lys Asn Gly Lys Asn Arg Arg Asn
1               5                   10                  15

Arg Lys Lys Lys Asn Trp Trp Trp
                20

<210> SEQ ID NO 145
<211> LENGTH: 17
<212> TYPE: PRT
<213> ORGANISM: Homo sapiens

<400> SEQUENCE: 145

Val Phe Arg Leu Lys Lys Trp Ile Gln Lys Val Ile Asp Gln Phe Gly
1               5                   10                  15

Glu

<210> SEQ ID NO 146
<211> LENGTH: 20
<212> TYPE: PRT
<213> ORGANISM: Artificial Sequence
<220> FEATURE:
<223> OTHER INFORMATION: Synthesized

<400> SEQUENCE: 146

Val Phe Arg Leu Lys Lys Trp Ile Gln Lys Val Ile Asp Gln Phe Gly
1               5                   10                  15

Glu Trp Trp Trp
                20

<210> SEQ ID NO 147
<211> LENGTH: 20
<212> TYPE: PRT
<213> ORGANISM: Homo sapiens

<400> SEQUENCE: 147

Ser Glu Lys Thr Leu Arg Lys Trp Leu Lys Met Phe Lys Lys Arg Gln
1               5                   10                  15

Leu Glu Leu Tyr
                20

<210> SEQ ID NO 148
<211> LENGTH: 23
<212> TYPE: PRT
<213> ORGANISM: Homo sapiens

<400> SEQUENCE: 148

Ser Glu Lys Thr Leu Arg Lys Trp Leu Lys Met Phe Lys Lys Arg Gln
1               5                   10                  15

Leu Glu Leu Tyr Trp Trp Trp
                20

<210> SEQ ID NO 149
<211> LENGTH: 22
<212> TYPE: PRT
<213> ORGANISM: Homo sapiens

<400> SEQUENCE: 149

Gln Pro Thr Arg Arg Pro Arg Pro Gly Thr Gly Pro Gly Arg Arg Pro
1               5                   10                  15

Arg Pro Arg Pro Arg Pro
                20

<210> SEQ ID NO 150
<211> LENGTH: 25

```
<212> TYPE: PRT
<213> ORGANISM: Artificial Sequence
<220> FEATURE:
<223> OTHER INFORMATION: Synthesized

<400> SEQUENCE: 150

Gln Pro Thr Arg Arg Pro Arg Pro Gly Thr Gly Pro Gly Arg Arg Pro
1               5                   10                  15

Arg Pro Arg Pro Arg Pro Trp Trp Trp
            20                  25

<210> SEQ ID NO 151
<211> LENGTH: 36
<212> TYPE: PRT
<213> ORGANISM: Artificial Sequence
<220> FEATURE:
<223> OTHER INFORMATION: Synthesized

<400> SEQUENCE: 151

Leu Leu Gly Asp Phe Phe Arg Lys Ser Lys Glu Lys Ile Lys Glu Phe
1               5                   10                  15

Lys Arg Ile Val Gln Arg Ile Lys Asp Phe Leu Arg Asn Leu Val Pro
            20                  25                  30

Arg Thr Glu Ser
        35

<210> SEQ ID NO 152
<211> LENGTH: 39
<212> TYPE: PRT
<213> ORGANISM: Artificial Sequence
<220> FEATURE:
<223> OTHER INFORMATION: Synthesized

<400> SEQUENCE: 152

Leu Leu Gly Asp Phe Phe Arg Lys Ser Lys Glu Lys Ile Lys Glu Phe
1               5                   10                  15

Lys Arg Ile Val Gln Arg Ile Lys Asp Phe Leu Arg Asn Leu Val Pro
            20                  25                  30

Arg Thr Glu Ser Trp Trp Trp
        35

<210> SEQ ID NO 153
<211> LENGTH: 12
<212> TYPE: PRT
<213> ORGANISM: Artificial Sequence
<220> FEATURE:
<223> OTHER INFORMATION: Synthesized

<400> SEQUENCE: 153

Ile Leu Arg Trp Pro Trp Trp Pro Trp Arg Arg Lys
1               5                   10

<210> SEQ ID NO 154
<211> LENGTH: 15
<212> TYPE: PRT
<213> ORGANISM: Artificial Sequence
<220> FEATURE:
<223> OTHER INFORMATION: Synthesized

<400> SEQUENCE: 154

Ile Leu Arg Trp Pro Trp Trp Pro Trp Arg Arg Lys Trp Trp Trp
1               5                   10                  15

<210> SEQ ID NO 155
<211> LENGTH: 8
```

```
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(8)
<223> OTHER INFORMATION: Xaa is Phe or is not present

<400> SEQUENCE: 155

Phe Phe Phe Xaa Xaa Xaa Xaa Xaa
1               5

<210> SEQ ID NO 156
<211> LENGTH: 8
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(8)
<223> OTHER INFORMATION: Xaa is Trp or is not present

<400> SEQUENCE: 156

Trp Trp Trp Xaa Xaa Xaa Xaa Xaa
1               5

<210> SEQ ID NO 157
<211> LENGTH: 8
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(8)
<223> OTHER INFORMATION: Xaa is Ile or is not present

<400> SEQUENCE: 157

Ile Ile Ile Xaa Xaa Xaa Xaa Xaa
1               5

<210> SEQ ID NO 158
<211> LENGTH: 8
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(8)
<223> OTHER INFORMATION: Xaa is Tyr or is not present

<400> SEQUENCE: 158

Tyr Tyr Tyr Xaa Xaa Xaa Xaa Xaa
1               5

<210> SEQ ID NO 159
<211> LENGTH: 8
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(8)
<223> OTHER INFORMATION: Xaa is Val or is not present

<400> SEQUENCE: 159

Val Val Val Xaa Xaa Xaa Xaa Xaa
```

```
<210> SEQ ID NO 160
<211> LENGTH: 6
<212> TYPE: PRT
<213> ORGANISM: Artificial Sequence
<220> FEATURE:
<223> OTHER INFORMATION: Synthesized

<400> SEQUENCE: 160

Trp Trp Tyr Tyr Ile Ile
1               5

<210> SEQ ID NO 161
<211> LENGTH: 4
<212> TYPE: PRT
<213> ORGANISM: Artificial Sequence
<220> FEATURE:
<223> OTHER INFORMATION: Synthesized

<400> SEQUENCE: 161

Trp Tyr Ile Val
1

<210> SEQ ID NO 162
<211> LENGTH: 6
<212> TYPE: PRT
<213> ORGANISM: Artificial Sequence
<220> FEATURE:
<223> OTHER INFORMATION: Synthesized

<400> SEQUENCE: 162

Tyr Tyr Val Val Phe Phe
1               5
```